United States Patent
Keel et al.

(10) Patent No.: US 8,162,841 B2
(45) Date of Patent: *Apr. 24, 2012

(54) STANDALONE SYSTEMIC ARTERIAL BLOOD PRESSURE MONITORING DEVICE

(75) Inventors: Allen J. Keel, San Jose, CA (US); Brian Jeffrey Wenzel, San Jose, CA (US); Edward Karst, S. Pasadena, CA (US); Wenbo Hou, Lancaster, CA (US); Taraneh Ghaffari Farazi, San Jose, CA (US); Timothy A. Fayram, Gilroy, CA (US); Eric S. Fain, Sunnyvale, CA (US); Paul A. Levine, Santa Clarita, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 431 days.

This patent is subject to a terminal disclaimer.

(21) Appl. No.: 12/474,276

(22) Filed: May 29, 2009

(65) Prior Publication Data

US 2009/0281399 A1    Nov. 12, 2009

Related U.S. Application Data

(63) Continuation-in-part of application No. 11/848,586, filed on Aug. 31, 2007.

(51) Int. Cl.
*A61B 5/02* (2006.01)
(52) U.S. Cl. ........ 600/486; 600/481; 600/500; 600/504; 600/513
(58) Field of Classification Search .................. 600/300, 600/481–486, 500–528; 607/115–138
See application file for complete search history.

(56) References Cited

U.S. PATENT DOCUMENTS

| | | | |
|---|---|---|---|
| 4,425,920 | A | 1/1984 | Bourland |
| 4,676,253 | A | 6/1987 | Newman |
| 4,791,931 | A | 12/1988 | Slate |
| 5,857,975 | A | 1/1999 | Golub |
| 5,862,805 | A | 1/1999 | Nitzan |
| 5,865,755 | A | 2/1999 | Golub |
| 6,120,459 | A | 9/2000 | Nitzan |

(Continued)

FOREIGN PATENT DOCUMENTS

EP    0256159 B1    5/1991

(Continued)

OTHER PUBLICATIONS

25, *Impedance Plethysmography*—http://www.bem.fi/book/25/25.htm.

(Continued)

*Primary Examiner* — Miranda Le
*Assistant Examiner* — Eric Messersmith
(74) *Attorney, Agent, or Firm* — Steven M. Mitchell

(57) ABSTRACT

Certain embodiments of the present invention are related to an implantable monitoring device to monitor a patient's arterial blood pressure, where the device is configured to be implanted subcutaneously. The device includes subcutaneous (SubQ) electrodes and a plethysmography sensor. Additionally, the device includes an arterial blood pressure monitor configured to determine at least one value indicative of the patient's arterial blood pressure based on at least one detected predetermined feature of a SubQ ECG and at least one detected predetermined feature of a plethysmography signal. Alternative embodiments of the present invention are directed to a non-implantable monitoring device to monitor a patient's arterial blood pressure based on features of a surface ECG and a plethysmography signal obtained from a non-implanted sensor.

29 Claims, 10 Drawing Sheets

U.S. PATENT DOCUMENTS

| | | | |
|---|---|---|---|
| 6,122,536 | A | 9/2000 | Sun |
| 6,409,675 | B1 * | 6/2002 | Turcott .................. 600/508 |
| 6,575,912 | B1 | 6/2003 | Turcott |
| 6,599,251 | B2 | 7/2003 | Chen |
| 6,647,287 | B1 | 11/2003 | Peel |
| 6,648,828 | B2 | 11/2003 | Friedman |
| 6,731,967 | B1 | 5/2004 | Turcott |
| 6,942,622 | B1 | 9/2005 | Turcott |
| 6,997,879 | B1 | 2/2006 | Turcott |
| 7,029,447 | B2 | 4/2006 | Rantala |
| 7,125,383 | B2 | 10/2006 | Hoctor |
| 7,212,861 | B1 | 5/2007 | Park |
| 7,286,875 | B1 | 10/2007 | Park |
| 2004/0030261 | A1 * | 2/2004 | Rantala .................. 600/561 |
| 2004/0167417 | A1 * | 8/2004 | Schulhauser et al. ......... 600/513 |
| 2005/0131306 | A9 | 6/2005 | Mills |
| 2005/0251059 | A1 | 11/2005 | Kim |
| 2005/0261593 | A1 * | 11/2005 | Zhang et al. .................. 600/485 |
| 2006/0074322 | A1 | 4/2006 | Nitzan |
| 2007/0276261 | A1 * | 11/2007 | Banet et al. .................. 600/481 |
| 2007/0276632 | A1 | 11/2007 | Banet |
| 2008/0039731 | A1 | 2/2008 | McCombie |
| 2008/0183083 | A1 * | 7/2008 | Markowitz et al. ........... 600/484 |
| 2008/0183232 | A1 | 7/2008 | Voss |
| 2008/0269624 | A1 * | 10/2008 | Zhang et al. .................. 600/508 |
| 2009/0216132 | A1 * | 8/2009 | Orbach .................. 600/485 |
| 2010/0185262 | A1 * | 7/2010 | Kuhn et al. .................. 607/60 |

FOREIGN PATENT DOCUMENTS

| | | |
|---|---|---|
| EP | 0443267 A1 | 8/1991 |
| EP | 0307093 B1 | 12/1995 |

OTHER PUBLICATIONS

Stewart et al., "Pseudo-QT Prolongation, Artifactual Electrocardiographic Patterns Produced by Transduction of Cardiovascular Motion," Pacing Clin. Electrophysiol., vol. 6 (Part 1), pp. 940-947 (Sep. 1983).

Allen, "Photoplethysmography and its Application in Clinical Physiological Measurement," Physiol. Meas. 28 (2007) R1-R39.

Chen et al., "Continuous Estimation of Systolic Blood Pressure Using the Pulse Arrival Time and Intermittent Calibration," Medical & Bilogical Engineering & Computing 2000, vol. 38, pp. 569-574.

Turcott et al., "Subcutaneous Photoplethysmography in Extravascular Hemodynamic Sensing," 47 pages.

Turcott et al., "Atrio-Ventricular Delay Optimization using Subcutaneous Photoplethysmography," 41 pages.

Payne et al., "Pulse Transit Time Measured from the ECG: An Unreliable Marker of Beat-to-Beat Blood Pressure," American Physiological Society, 2006, pp. 136-141.

Poon et al., "Cuff-less and Noninvasive Measurements of Arterial Blood Pressure by Pulse Transit Time," IEEE 2005, Engineering in Medican and Biology 27th Annual Conference, pp. 5877-5880.

Sameshima et al., "Continuous Systolic Blood Pressure Monitoring by the Difference in Electrocardiogram and Pulse Oximetry in Near-Term, Exteriorized Goat Fetuses," Journal of the Society for Gynecologic Investigation 2003; 10; 200; 6 pages.

\* cited by examiner

STANDALONE SYSTEMIC ARTERIAL BLOOD PRESSURE MONITORING DEVICE

PRIORITY CLAIM

This application is a continuation-in-part (CIP) and claims priority to U.S. patent application Ser. No. 11/848,586, filed Aug. 31, 2007, which is incorporated herein by reference.

FIELD OF THE INVENTION

Embodiments of the present invention relate to devices for monitoring arterial blood pressure, and methods for use therewith.

BACKGROUND OF THE INVENTION

A person's circulatory system includes both systemic and pulmonary circulation systems. Pulmonary circulation supplies the lungs with blood flow, while the systemic circulation takes care of all the other parts of the body. The heart serves as a pump that keeps up the circulation of the blood. Both the pulmonary and systemic circulatory systems are made up of arteries, arterioles, capillaries, venules and veins. The arteries take the blood from the heart, while the veins return the blood to the heart Blood pressure is defined as the force exerted by the blood against any unit area of the vessel wall. The measurement unit of blood pressure is millimeters of mercury (mmHg). Pulmonary and systemic arterial pressures are pulsatile, having systolic and diastolic pressure values. The highest recorded pressure reading is called systolic pressure, which results from the active contraction of the ventricle. Although the arterial pressure and indeed flow in the arteries is pulsatile, the total volume of blood in the circulation remains constant. The lowest pressure reading is called diastolic pressure which is maintained by the resistance created by the smaller blood vessels still on the arterial side of the circulatory system (arterioles). Stated another way, the systolic pressure is defined as the peak pressure in the arteries, which occurs near the beginning of a cardiac cycle. In contrast, the diastolic pressure is the lowest pressure, which occurs at the resting phase of the cardiac cycle. The pulse pressure reflects the difference between the maximum and minimum pressures measured (i.e., the difference between the systolic pressure and diastolic pressure). The mean arterial pressure is the average pressure throughout the cardiac cycle.

Arterial pulse pressure, such as mean arterial pressure (MAP), is a fundamental clinical parameter used in the assessment of hemodynamic status of a patient. Mean arterial pressure can be estimated from real pressure data in a variety of ways. Among the techniques that have been proposed, two are presented below. In these formulas, SP is the systolic blood pressure, and DP is diastolic pressure.

a. $MAP_2(SP+2DP)/3 = \frac{1}{3}(SP) + \frac{2}{3}(DP)$ b. $Map_1 = (SP+DP)/2$

Systolic pressure and diastolic pressure can be obtained in a number of ways. A common approach is to use a stethoscope, an occlusive cuff, and a pressure manometer. However, such an approach is slow, requires the intervention of a skilled clinician and does not provide timely readings as it is a measurement at only a single point in time. While systolic pressure and diastolic pressure can also be obtained in more automated fashions, it is not always practical to obtain measures of pressure using a cuff and pressure transducer combination, especially if the intention or desire is to implant a sensor that can monitor arterial pressure on a chronic basis.

Another approach for obtaining measures of arterial pressure is to use an intravascular pressure transducer. However, an intravascular device may cause problems, such as, embolization, nerve damage, infection, bleeding and/or vessel wall damage. Additionally, the implantation of an intravascular lead requires a highly skilled physician such as a surgeon, electrophysiologist, or interventional cardiologist.

Plethysmography, the measurement of volume of an organ or body part, has a history that extends over 100 years. Photoplethysmography (PPG) uses optical techniques to perform volume measurements, and was first described in the 1930s. While best known for their role in pulse oximetry, PPG sensors have also been used to indirectly measure blood pressure. For example, non-invasive PPG sensors have been used in combination with in an inflatable cuff in a device known as Finapres. U.S. Pat. Nos. 4,406,289 (Wesseling et al.) and 4,475,940 (Hyndman) are exemplary patents that relate to the Finapres technique. The cuff is applied to a patient's finger, and the PPG sensor measures the absorption at a wavelength specific for hemoglobin. After the cuff is used to measure the individual's mean arterial pressure, the cuff pressure around the finger is then varied to maintain the transmural pressure at zero as determined by the PPG sensor. The Finapres device tracks the intra-arterial pressure wave by adjusting the cuff pressure to maintain the optical absorption constant at all times.

There are a number of disadvantages to the Finapres technique. For example, when there exists peripheral vasoconstriction, poor vascular circulation, or other factors, the blood pressure measured in a finger is not necessarily representative of central blood pressure. Further, maintaining continuous cuff pressure causes restriction of the circulation in the finger being used, which is uncomfortable when maintained for extended periods of time. Accordingly, the Finapres technique is not practical for chronic use. Additionally, because of the need for a pneumatic cuff, a Finapres device can not be used as an implanted sensor.

Simple external blood pressure monitors also exist, but they do not offer continuous measurement and data logging capability. These devices can be purchased at a drug store, but patient compliance is required to make regular measurements and accurately record the data. Additionally, portable external miniature monitors that automatically log blood pressure data exist, but these devices can only store a day or so of data and require clinician interaction to download and process the measured data.

As is evident from the above description, there is the need for improved systems and methods for monitoring arterial blood pressure, including systolic pressure, diastolic pressure and mean arterial pressure.

SUMMARY OF THE INVENTION

Certain embodiments of the present invention are related to an implantable monitoring device to monitor a patient's arterial blood pressure, where the device is configured to be implanted subcutaneously. Such an implantable device includes subcutaneous (SubQ) electrodes configured to obtain a subcutaneous electrocardiogram (SubQ ECG) that is indicative of electrical activity of the patient's heart. Additionally, the implantable device includes a plethysmography sensor configured to obtain a plethysmography signal indicative of changes in the patient's arterial blood volume. Further, the implantable device includes an arterial blood pressure monitor configured to detect one or more predetermined feature of the SubQ ECG signal and to detect one or more predetermined feature of the plethysmography signal. The arterial blood pressure monitor is also configured to determine at least one value indicative of the patient's arterial blood pressure based on at least one detected predetermined feature of the SubQ ECG and at least one detected predetermined feature of the plethysmography signal. The at least one value indicative of the patient's arterial blood pressure can be indicative of diastolic pressure (DP), systolic pressure (SP), pulse pressure (PP), mean arterial pressure (MAP), a change in DP, a change in SP, a change in PP and/or a change in MAP. More generally, the arterial blood pressure monitor can be configured to monitor changes in the patient's arterial blood pressure based on changes in the determined at least one value indicative of the patient's arterial blood pressure.

In accordance with certain embodiments, the implantable monitoring device is configured to transfer the at least one value indicative of the patient's arterial blood pressure to a non-implanted device, e.g., using telemetry. Additionally, in accordance with certain embodiments, the implantable monitoring device is not configured to pace the patient's heart and is not configured to defibrillate the patient's heart.

In accordance with certain embodiments, the implantable monitoring device includes a housing within which the arterial blood pressure monitor is located. The subQ electrodes can be attached to the housing, e.g., substantially flush with and/or adjacent to the housing. Alternatively, the subQ electrodes can be remote from the housing and be configured to be mounted subcutaneously outside of a patient's rib cage.

In accordance with certain embodiments, the plethysmography sensor is within, integral with or attached to the housing. For example, the plethysmography sensor can be a photoplethysmography (PPG) sensor configured to obtain a photoplethysmography (PPG) signal indicative of changes in arterial blood volume, where the PPG sensor includes a light source and a light detector. The light source and the light detector can be within, integral with or attached to the housing. The light source and light detector can be used to detect changes in arterial blood volume of patient tissue adjacent the housing. Alternatively, optical fibers can be used to transmit light produced by the light source to a portion of the patient's body that is remote from the housing, and to provide a portion of the transmitted light reflected from and/or transmitted through the portion of the patient's body to the light detector, thereby enabling detection of changes in arterial blood volume of patient tissue remote from the housing. In other embodiments, a PPG sensor can include a light source and a light detector that are located within, integral with or attached to a lead that extends from the housing to thereby enable the light source and light detector to be placed in a portion of the patient's body that is remote from the housing, also enabling detection of changes in arterial blood volume of patient tissue remote from the housing. The light source can include, e.g., one or more light-emitting diodes (LEDs), organic light emitting diodes (OLEDs), incandescent lamps, laser diodes, or the like. The light detector can include, e.g., one or more photoresistors, photodiode, phototransistors, photodarlingtons, avalanche photodiodes, or the like.

In certain embodiments, the arterial blood pressure monitor is configured to determine a pulse arrival time (PAT) value by determining a time from a detected predetermined feature of the SubQ ECG signal to a detected predetermined feature of the PPG signal. At least one value indicative of the patient's arterial blood pressure can then be determined based on the PAT value. For example, the arterial blood pressure monitor can determine a value indicative of systolic pressure (SP) based on the PAT value. In alternative embodiments, instead of determining a pulse arrival time (PAT), a peak pulse arrival time (PPAT) is determined, and the value indicative of systolic pressure (SP) is determined based on the PPAT. Additionally, the arterial blood pressure monitor can determine a peak-to-peak amplitude of the plethysmography signal, and determine a value indicative of diastolic pressure (DP) based on the peak-to-peak amplitude and the value indicative of SP. For a more specific example, a value indicative of pulse pressure (PP) can be determined based on the peak-to-peak amplitude, and the value indicative of DP can be determined by subtracting the value indicative of PP from the value indicative of SP. Additionally, a value indicative of mean arterial pressure (MAP) can be determined based on the Value indicative of SP and the Value indicative of DP, e.g., using the equation $$MAP_2(SP+2DP)/3 = \frac{1}{3}(SP) + \frac{2}{3}(DP).$$

Alternative embodiments of the present invention are directed to a non-implantable monitoring device to monitor a patient's arterial blood pressure. The device can include surface electrodes that can be worn against the patient's skin (instead of being implanted) so that a surface electrocardiogram (surface ECG) that is indicative of electrical activity of the patient's heart can be obtained. An arterial blood pressure monitor can be located within a non-implantable housing, and can be configured to monitor arterial blood pressure in a similar manner as the implanted device. In certain embodiments, the surface ECG electrodes can be attached to the housing, e.g., substantially flush with and/or adjacent to the housing. In such embodiments, the housing can be worn against a patient's skin. In other embodiments, the surface ECG electrodes can be remote from the housing and at least some of the electrodes can be configured to be mounted on a patient's skin outside of a patient's rib cage. In some embodiments the plethysmography sensor (e.g., PPG sensor) of the non-implantable monitoring device can be within, integral with or attached to the housing (e.g., a light source and a light detector can be within, integral with or attached to the housing). In such embodiments, the light source and detector can face the patients skin that is adjacent the housing. Alternatively, optical fibers can be used to transmit light produced by the light source to a portion of a patient's body that is remote from the housing, and can provide a portion of the transmitted light reflected from and/or transmitted through the portion of the patient's body to the light detector. In still other embodiments, the PPG sensor can includes a light source and a light detector that are located within, integral with or attached to the lead that extends from the housing to thereby enable the light source and light detector to be placed adjacent a portion of the patient's body (e.g., a finger, earlobe, etc) that is remote from the device housing.

Additional and alternative embodiments, features and advantages of the invention will appear from the following description in which the preferred embodiments have been set forth in detail, in conjunction with the accompanying drawings and claims.

DETAILED DESCRIPTION OF THE INVENTION

Figure 1A:
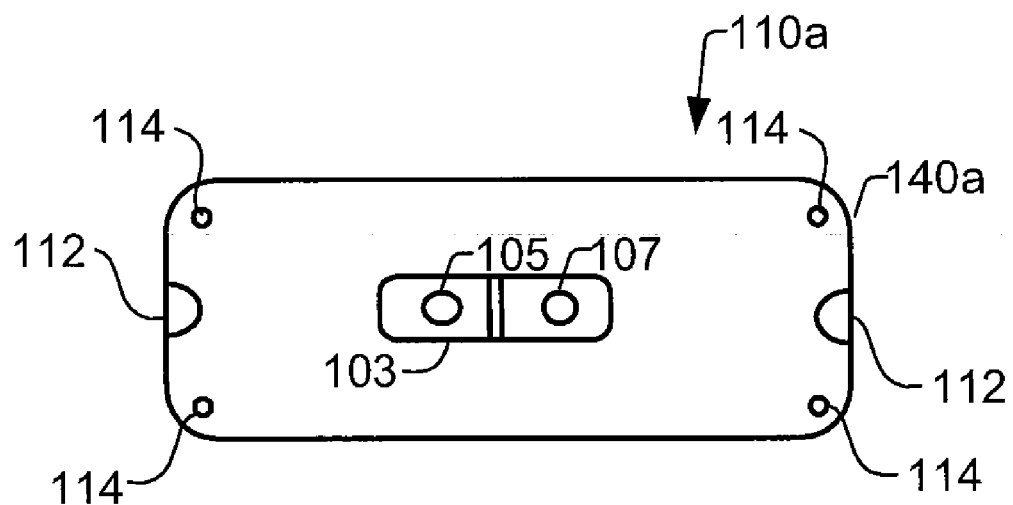
FIGS. 1A and 1B illustrate an implantable standalone blood pressure monitoring devices that include a PPG sensor and SubQ electrodes, according to specific embodiments of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

Figure 1B:
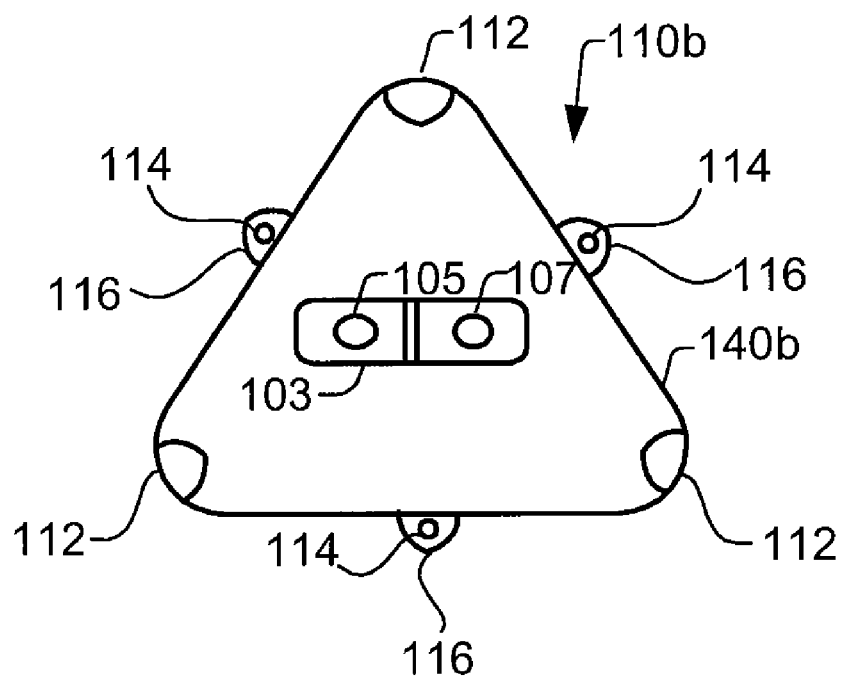

FIGS. 1A and 1B will now be used to describe implantable standalone arterial blood pressure monitoring devices that can be used to determine values indicative of arterial blood pressure, in accordance with embodiments of the present invention. As will be described in more detail below with reference to the flow diagrams of FIGS. 4A and 4B, the devices of FIGS. 1A and 1B, and FIGS. 1C-1F, can be used to obtain a subcutaneous electrocardiogram (SubQ ECG) signal indicative of electrical activity of the patient's heart and a plethysmography signal (e.g., a PPG signal) indicative of changes in arterial blood volume, and based thereon, can monitor a patient's arterial blood pressure, including changes therein.

Referring to FIGS. 1A and 1B, implantable standalone arterial blood pressure monitoring devices 110 are shown as including subQ electrodes 112, which can be used to obtain SubQ ECG signals. The implantable devices 110 also include an implantable PPG sensor 103 that can be used to produce a PPG signal, similar to signal 310 shown in FIG. 3. Additional details of the PPG sensor 103 are discussed below. In accordance with an embodiment, the device 110 includes suture holes 114 for fixation of the device 110 to patient tissue, which is useful for obtaining a high quality signal by reducing motion artifacts and applying a consistent contact force at the site of the optics to improve optical coupling with tissue. The suture holes 114 can be openings through the housing 140 (e.g., as shown in FIG. 1A), or the suture holes can be openings through tabs 116 that extend from the housing 140 (e.g., as shown in FIG. 1B). Other locations of the holes 114 and/or the tabs 116 are possible, and within the scope of the present invention. Although not shown in FIGS. 1C-1F, similar suture holes 114 can be included in the implanted devices 110 shown therein.

In the embodiments of FIGS. 1A and 1B, the subQ electrodes 112 (also referred to as ECG electrodes) are located on the housing 140, and more specifically, the subQ electrodes are substantially flush with and/or adjacent to the housing 140. The housing 140 can be made of a metal or other conductive material, in which case, the electrodes 112 should be electrically isolated from the housing 140. Alternatively, the housing 140 can be made from a non-conductive material, e.g., a plastic or other polymer. In embodiments, the devices 110 are not capable of pacing and not capable of defibrillation, but rather, the implantable devices 110 are primarily for monitoring purposes. This is why such devices can be referred to as standalone arterial blood pressure monitors.

In FIG. 1A, the oblong geometry of the housing 140a can be used to maximize separation of electrodes 112 and prevent rotation of the device within a tissue pocket, thereby allowing interpretation of morphology features in an ECG sensed using the electrodes 112. While two subQ electrodes 112 are shown, more can be present. The housing 140 is preferably small and thin, with smooth surfaces and a physiologic contour that minimizes tissue trauma and inflammation. If desired, though not necessary, sutures or some other fixation means can be used to fix the housing 140 at a specific implanted location.

FIG. 1B illustrates an embodiment where the housing 140b is a different shape, and which includes an additional subQ electrode 112. In the embodiment illustrated in FIG. 1B, three subQ electrodes 112 are present, one at each apex of the triangle formed by the device housing 140. If the device is implanted with an appropriate orientation, these three electrodes may allow the three standard surface ECG leads I-III to be approximated. In another embodiment, four or more ECG electrodes 112 might be used. U.S. Pat. No. 6,409,675 (Turcott), which is incorporated herein by reference, in its discussion of FIG. 2a-2c and 3a-3c provides some additional details of an implantable monitor that includes ECG electrodes on its housing and a PPG sensor.

Figure 1C:
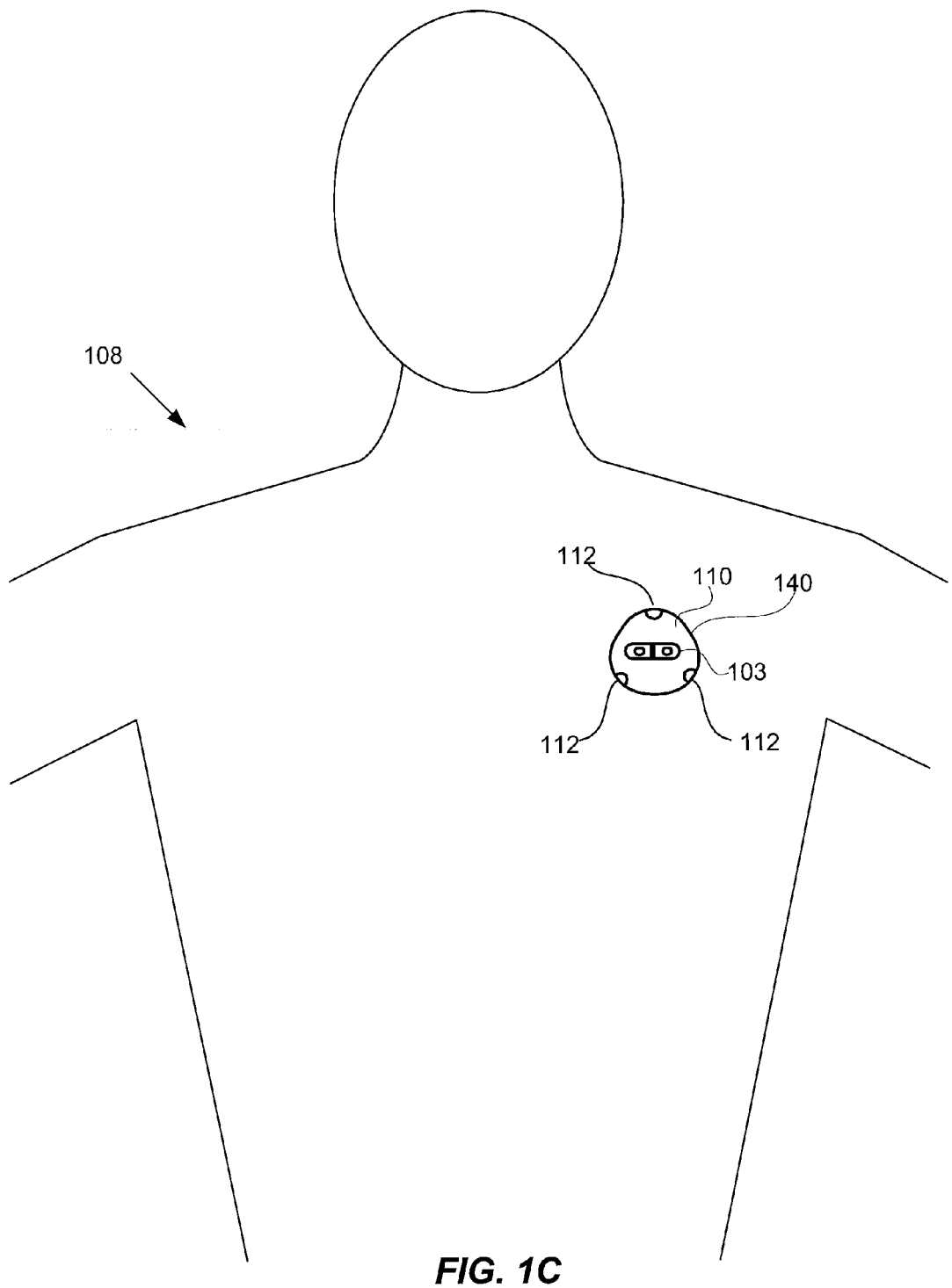
FIG. 1C is used to illustrate that an implantable standalone blood pressure monitoring device, according to an embodiment of the present invention, can be implanted subcutaneously in a patient's pectoral region.

FIG. 1C illustrates an implantable standalone arterial blood pressure monitoring device 110 of an embodiment of the present invention (where the device is the same or similar to the device 110b of FIG. 1B), implanted in a subcutaneous pectoral region of a patient 108. An alternatively location where the device 110 can be implanted includes, but is not limited to, a subcutaneous abdominal region.

Figure 1D:
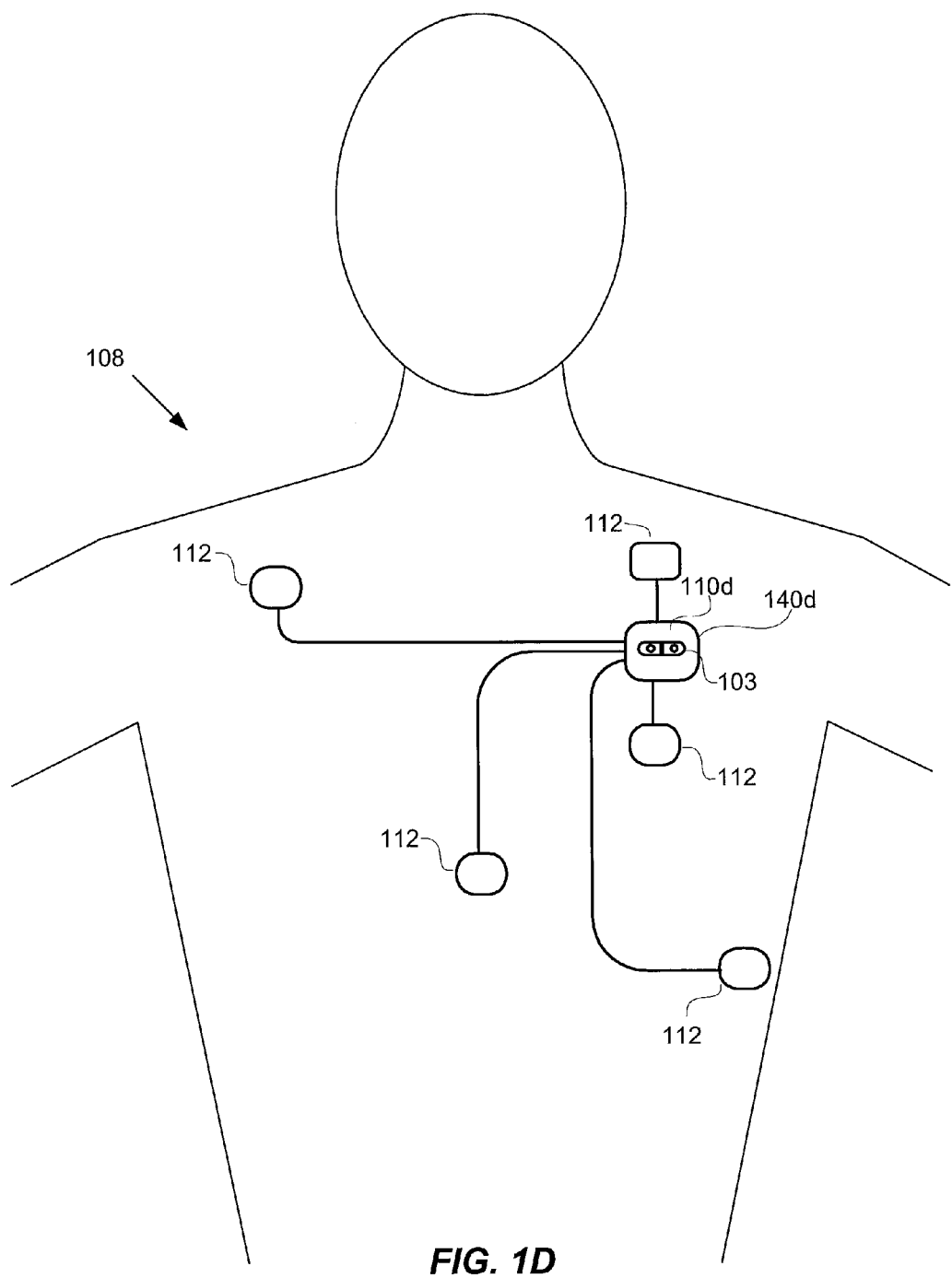
FIG. 1D is used to illustrate an implantable standalone blood pressure monitoring device, according to an embodiment of the present invention, that includes subcutaneous electrodes that are remote from the device housing.

FIG. 1D illustrates an alternative embodiment where the subQ electrodes 112 are remote from the housing, yet are still extracardiac. While the device 110d shown in FIG. 1D may not be as easy and fast to implant as the devices 110 shown in FIGS. 1A-1C, since the device 110d and electrodes 112 in FIG. 1D are still extracardiac and subcutaneous, the device 110d and remote subQ electrodes 112 can still be implanted relatively easily and quickly. In the embodiment of FIG. 1D, the subQ extracardiac electrodes 112 are preferably extravascular and can be, e.g., paddle electrodes mounted subcutaneously outside of the rib cage, but are not limited thereto. Exemplary locations of the subQ extracardiac electrodes 112 include near the bottom of the sternum (slightly to the left), below the left pectoral area, and below the clavicle and on the back left side (just below the shoulder blade). Additional and/or alternative locations for subQ electrodes 112 are also within the scope of the present invention. Also, while one or more electrodes 112 can be remote from the housing 140, as shown in FIG. 1D, one or more electrodes can be on the housing 140 (e.g., substantially flush with and/or adjacent to the housing 140), as was discussed above with reference to FIGS. 1A and 1B, and/or a conductive housing 140 can act as one of the electrodes.

Figure 1E:
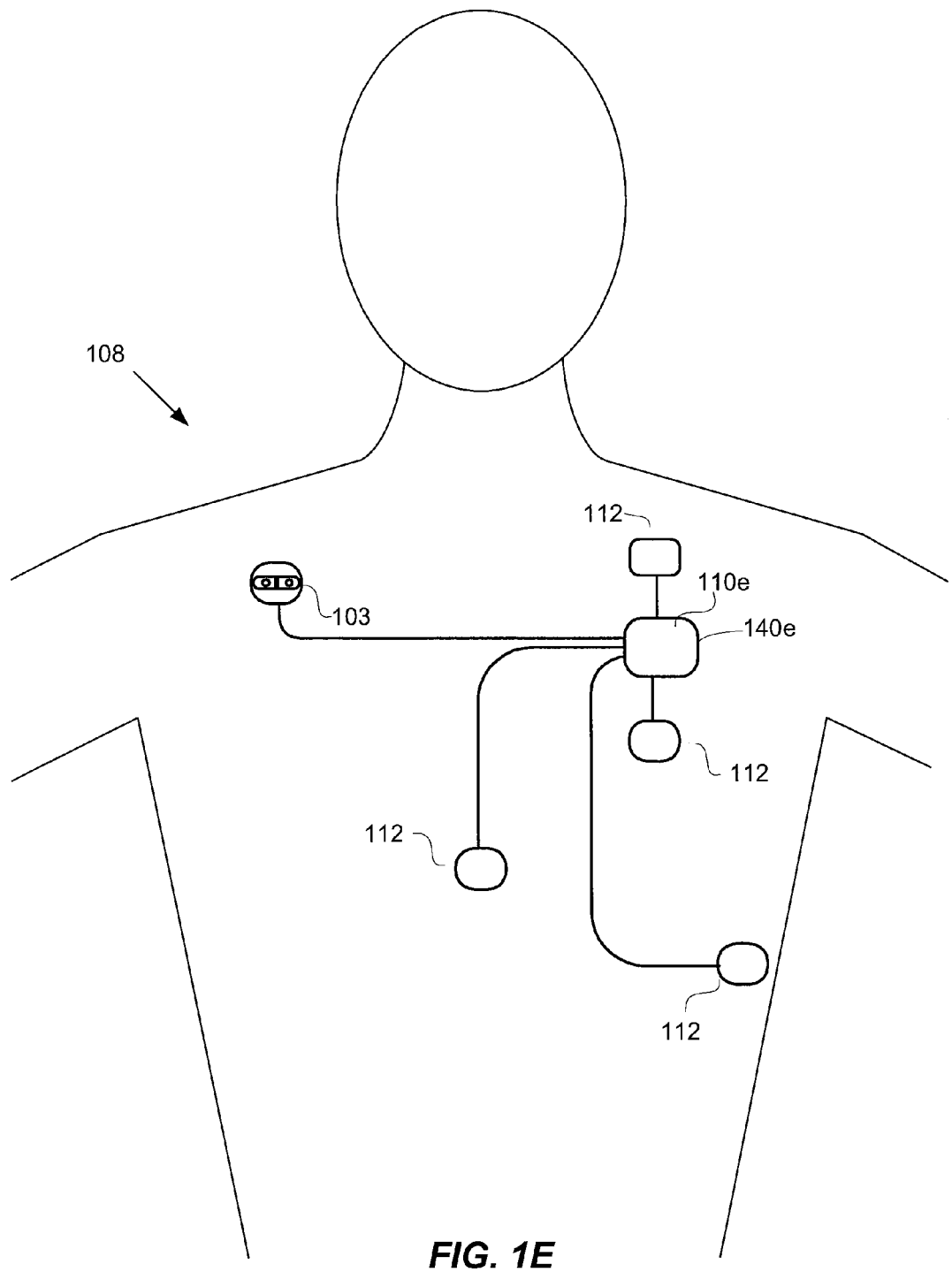
FIG. 1E is used to illustrate an implantable standalone blood pressure monitoring device, according to an embodiment of the present invention, that includes a PPG sensor that is remote from the device housing and SubQ electrodes that are remote from the device housing.

FIG. 1E is used to illustrate an embodiment where the PPG sensor 103 is remote from the housing 140 of the device 110e, but communicates with the electronics in the device housing 140 via one or more wires, optical fibers, or wirelessly (e.g., using telemetry, RF signals and/or using body fluid as a communication bus medium). This embodiment enables an obtained PPG signal to be indicative of changes in arterial blood volume at a location remote from the device housing 140. If desired, multiple PPG signals can be obtained, e.g., using multiple PPG sensors at different locations. In this embodiment, the electrodes 112 can be paddle electrodes similar to those discussed above with reference to FIG. 1D, and/or the electrodes 112 can be on the housing 140 (e.g., substantially flush with and/or adjacent to the housing 140), as was discussed above with reference to FIGS. 1A and 1B, and/or a conductive housing 140 can act as one of the electrodes.

Figure 1F:
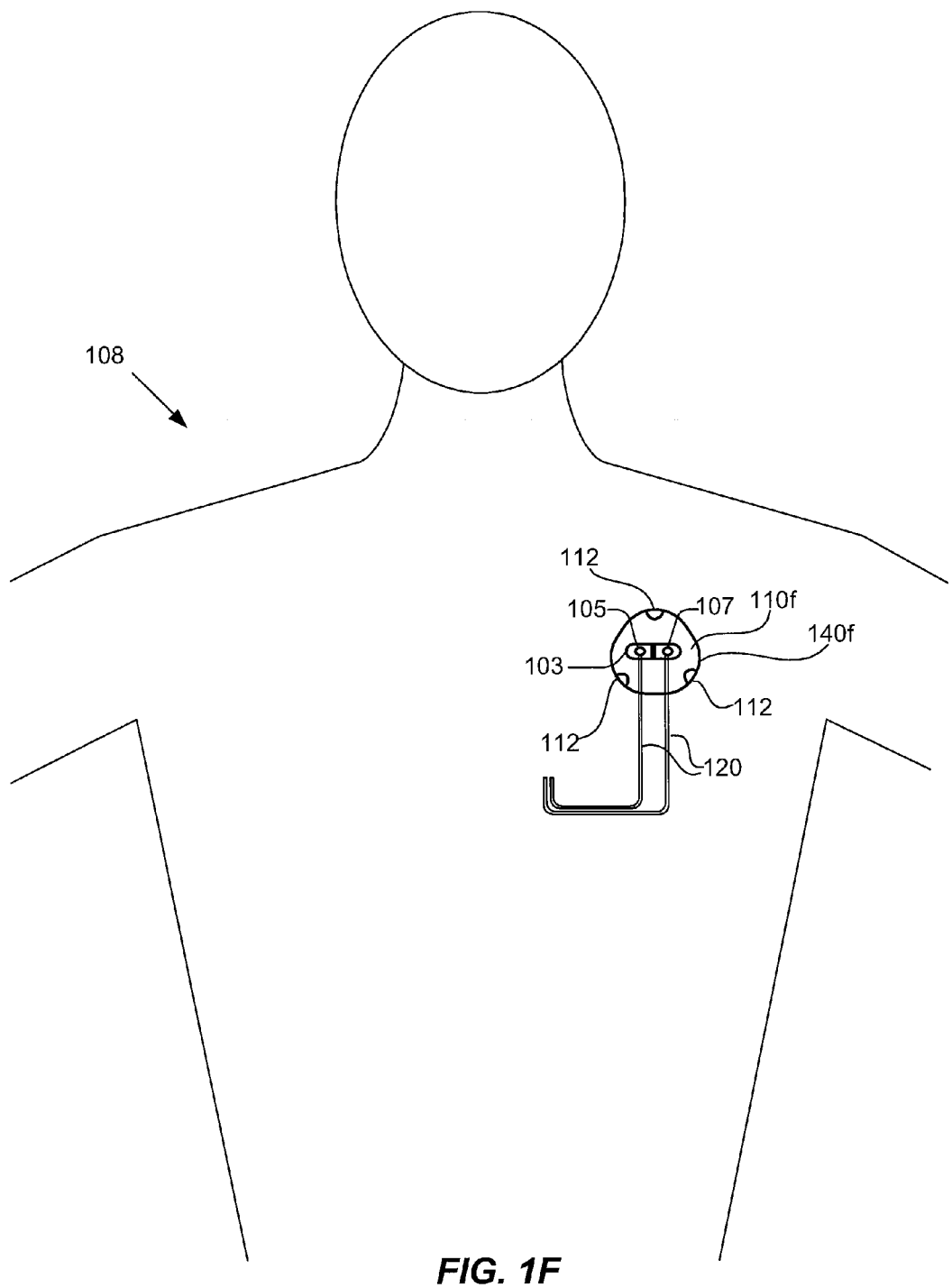
FIG. 1F is used to illustrate an implantable standalone blood pressure monitoring device, according to an embodiment of the present invention, that includes fiber optics that are used to transmit light into and detect light from patient tissue that is remote from the device housing.

FIG. 1F is used to illustrate an implantable standalone blood pressure monitoring device 110f, according to an embodiment of the present invention, that includes optical fibers 120 that are used to transmit light into and detect light from tissue that is remote from the device housing, even though the light source and light detector are located within or adjacent the device housing 140. This embodiment enables an obtained PPG signal to be indicative of changes in arterial blood volume at a location remote from the device housing 140, even though the light source 105 and light detector 107 are not remote from the housing. In certain embodiments, the optical fibers 120 can be tunneled to the aorta, which would increase the accuracy of the PPG signal and lead to better blood pressure estimates. The optical fibers 120 can tunneled to other locations which can be intracardiac or extracardiac. The distal end of the optical fiber(s) associated with the light source can be generally parallel to the distal end of the optical fiber(s) associated with the light detector, so that the light detector detects the portion of light reflected from tissue. Alternatively, the distal end of the optical fiber(s) associated with the light source can generally face the distal end of the optical fiber(s) associated with the light detector, with tissue therebetween, so that the light detector detects the portion of light transmitted through (as opposed to reflected from) the tissue therebetween.

Figure 1G:
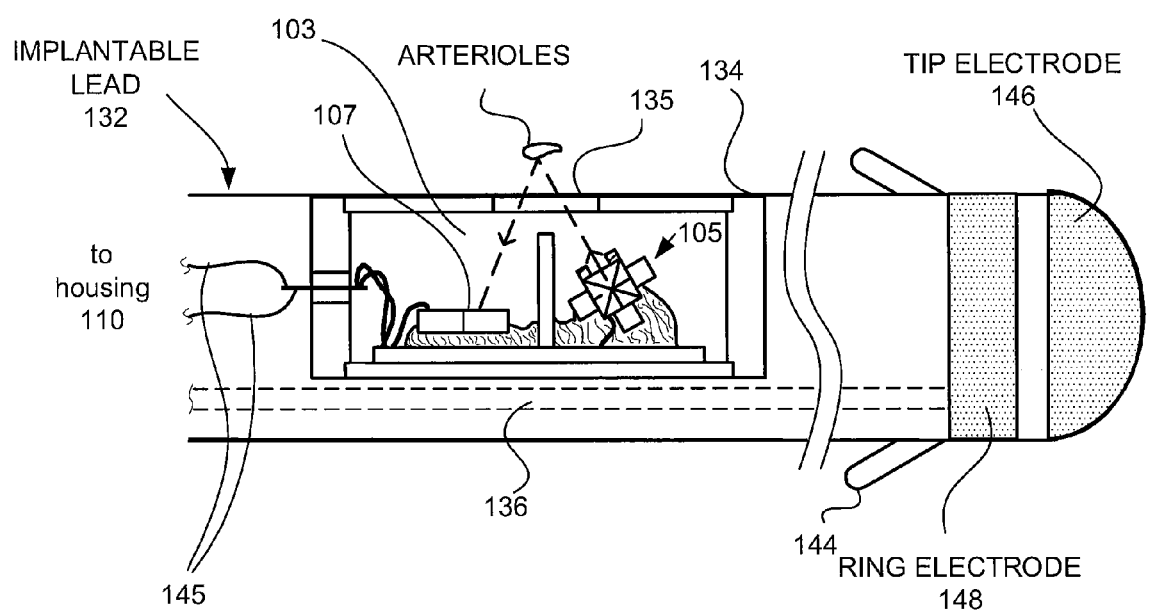
FIG. 1G is used to illustrate a PPG sensor within or attached to a lead that can extend from an implantable standalone blood pressure monitoring device housing, according to an embodiment of the present invention.

FIG. 1G is used to illustrate an embodiment where a PPG sensor 103 is within or attached to a lead 132 that may extend from a main device housing (not shown in FIG. 1G, but which can be similar to the housings 140 shown in other FIGS.) within which is located a microprocessor, memory, battery, alarm, and/or the like. Referring to FIG. 1G, a PPG sensor module 103 is shown as being built into an implantable lead 132. Accordingly, in this embodiment, a housing 134 of the sensor module 103 is sized to fit within the implantable lead 132. Here, the height and depth (or diameter) of the sensor module 103 can each be about 4 mm or less, and preferably about 3 mm. The length of the sensor module 103, which extends axially in the lead 132 can be somewhat larger, because the length of the lead 132 is relatively large as compared to the diameter of the lead. The PPG sensor 103 is preferably located proximal from the distal tip of the lead 132 so that the PPG sensor 103 is sufficiently remote from the heart that variations in pulse transmission time are detectable and meaningful.

The portion of the lead 132 that is adjacent to a window 135 of the sensor module, where light is to exit and enter, should allow the light to pass in and out of the sensor 103. Thus, the lead 132 may be transparent, or include its own window, opening, or the like. The lead 132 is shown as including tines 144 for attaching the lead in its desired position, but may include any other type of fixation means (e.g., a pigtail shaped fixation means), or none at all. The lead 132 can also have a suture sleeve, that enables the lead to be sutured to patient tissue. Additionally, the lead 132 may also include a lumen 136 for a stylet, which can be used for guiding the lead to its desired position. Also shown in FIG. 1G are wires 145 that provide power and possibly control signals to the sensor 130 and provide PPG signals from the sensor 130 to circuitry within an implantable device main housing. This embodiment enables an obtained PPG signal to be indicative of changes in arterial blood volume at a location remote from the device housing 140 by tunneling the lead to a desired location. In certain embodiments, the lead 132 can be tunneled to the aorta, which would increase the accuracy of the PPG signal and lead to better blood pressure estimates. The lead 132 can tunneled to other locations which can be intracardiac or extracardiac. As shown in FIG. 1G, the lead can also include one or more electrodes 146, 148 that can be used to obtain an ECG. Additional details of a lead that includes an optical sensor that can be used to produce a PPG signal are provided in U.S. patent application Ser. No. 11/231,555, entitled "Improved Multi-Wavelength Implantable Oximeter Sensor" (Poore), filed Sep. 20, 2005, and U.S. patent application Ser. No. 11/282,198, entitled "Implantable Device with a Calibration Photodetector" (Poore), filed Nov. 17, 2005.

Figure 3:
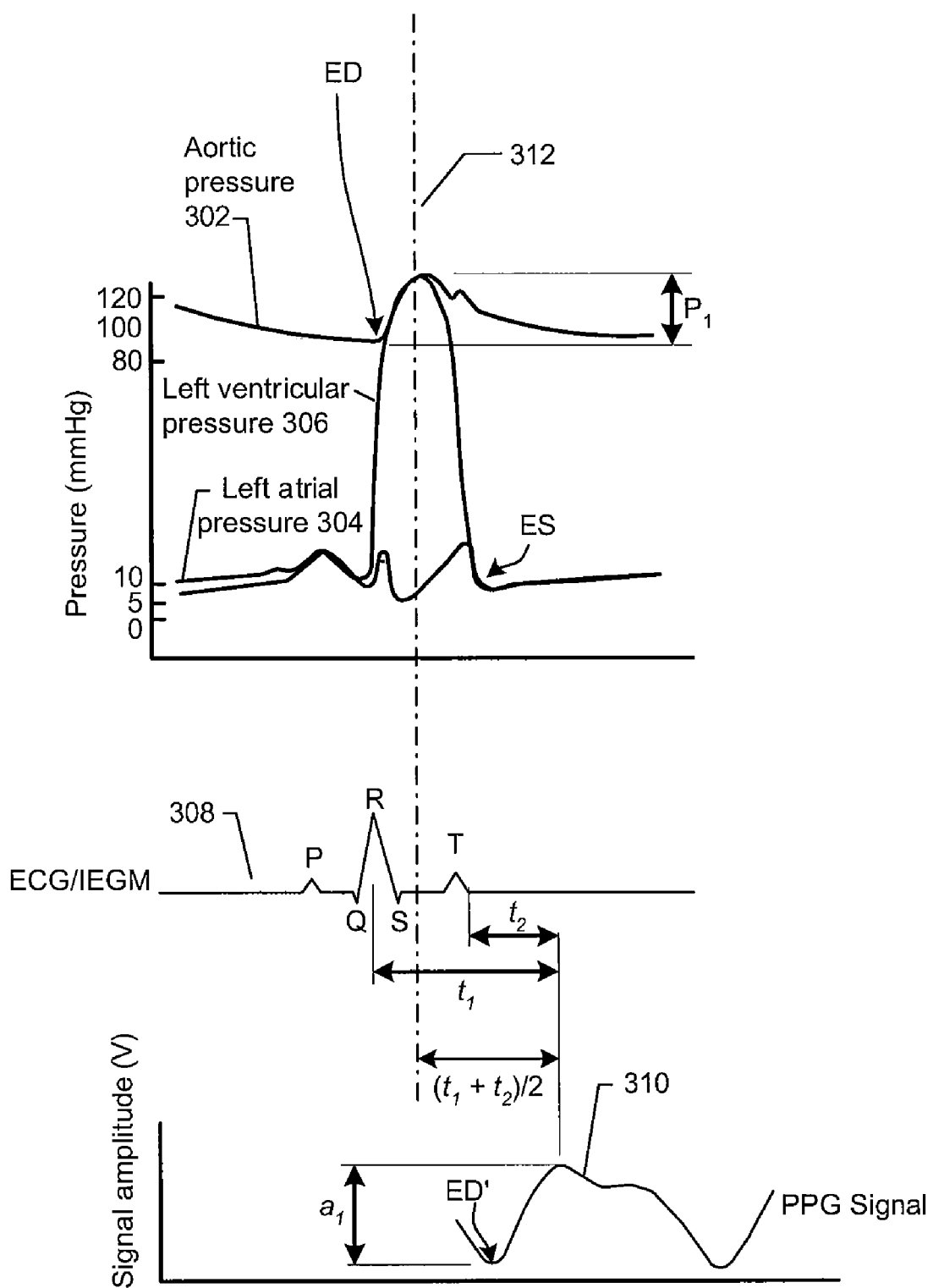
FIG. 3 includes signal waveforms that are used to show the relative timing of electrical and mechanical cardiac events that occur during a cardiac cycle. The upper graph includes an aortic pressure waveform, a left atrial pressure waveform and a left ventricular pressure waveform. The middle graph includes a subcutaneous electrocardiogram (subQ ECG) signal indicative of electrical cardiac activity. The lower graph includes a photoplethysmography (PPG) signal, which is indicative of indicative of changes in a patient's arterial blood volume.

As mentioned above, in various embodiments the implantable devices 110 of FIGS. 1A-1G include an implantable photoplethysmography (PPG) sensor 103 that can be used to produce a PPG signal, similar to signal 310 shown in FIG. 3. Referring back to FIGS. 1A-1G, the PPG 103 sensor includes a light source 105 and a light detector 107. The light source 105 can include, e.g., one or more light-emitting diodes (LEDs), organic light emitting diodes (OLEDs), incandescent lamps, laser diodes, and the like. The light detector 107 can include, e.g., one or more photoresistors, photodiode, phototransistors, photodarlingtons, avalanche photodiodes, or the like. Light detectors are often also referred to as photodetectors or photocells.

In certain embodiments, the light source 105 outputs light that is reflected or backscattered by surrounding patient tissue, and reflected/backscattered light is received by the light detector 107. In this manner, changes in reflected light intensity are detected by the light detector, which outputs a signal indicative of the changes in detected light. Alternatively, if the light source 105 and light detector 107 face one another with patient tissue therebetween, light that gets transmitted through patient tissue is detected by the light detector, again with changes in light intensity being detected by the light detector, which outputs a signal indicative of the changes in detected light. The output of the light detector can be filtered and amplified. The signal can also be converted to a digital signal using an analog to digital converter, if the PPG signal is to be analyzed in the digital domain. Additional details of exemplary implantable PPG sensors are disclosed in U.S. Pat. Nos. 6,409,675 and 6,491,639, both entitled "Extravascular Hemodynamic Sensor" (both Turcott), which are incorporated herein by reference.

A PPG sensor can use a single wavelength of light, a combination of several discrete wavelengths or a broad spectrum of many wavelengths. It is generally the output of the light detector that is used to produce a PPG signal. However, techniques have also been disclosed where the output of the light detector is maintained relatively constant by modulating the drive signal used to drive the light source, in which case the PPG signal is produced using the drive signal, as explained in U.S. Pat. No. 6,731,967, entitled "Methods and Devices for Vascular Plethysmography via Modulation of Source Intensity," (Turcott), which is incorporated herein by reference.

The PPG sensor 103 can be attached to a housing 140 of an implantable device. Exemplary details of how to attach a PPG sensor module to a device housing are described in U.S. patent application Ser. No. 10/913,942, entitled "Autonomous Sensor Modules for Patient Monitoring" (Turcott et al.), filed Aug. 4, 2004, which is incorporated herein by reference. It is also possible that the PPG sensor 103 be integrally part of the implantable device 110. For example, the PPG sensor 103 can be located within the housing 140, and the housing can have a window through which light can be transmitted and detected. In a specific embodiment, the PPG sensor 103 has a titanium frame with a light transparent quartz window that can be welded into a corresponding slot cut in the device housing 140. This will insure that the enclosure with the welded PPG sensor will maintain a hermetic condition.

Where the PPG sensor is incorporated into or attached to the housing 140 of the device 110, the light source 105 and the light detector 107 can be mounted adjacent to one another. The light source 105 and the light detector 107 can be placed on the side of the implantable device 110 that, following implantation, faces the chest wall (i.e., inward, away from the skin of the patient), and can be configured such that light cannot pass directly from the source to the detector. The placement on the side of the device 110 that faces the chest wall is believed to maximize the signal to noise ratio by directing the signal toward the highly vascularized musculature, and shielding the source and detector from ambient light that enters the body through the skin. Alternatively, at the risk of increasing susceptibility to ambient light, the light source 105 and the light detector 107 can be placed on the face of the device 110 that faces the skin of the patient. Other locations of the light source 105 and light detector 107 relative to the device housing are possible and within the scope of the present invention.

The implantable PPG sensor 103 can output a PPG signal similar to signal 310 shown in FIG. 3. More specifically, the output of the light detector 105 can be an analog signal that resembles signal 310. Such a signal can be filtered, amplified and/or averaged as appropriate, e.g., to remove respiratory affects on the signal, and the like. Additionally, the signal can be digitized using an analog to digital converter. Based on the PPG signal, and a subQ ECG obtained using implanted electrodes 112, times $t_1$, $t_2$ and peak-to-peak amplitude $a_1$, which are discussed below with reference to FIGS. 3, 4A and 4B, can be determined, thereby enabling measures of SP, DP and MAP to be determined in the manners described below. Additional features of the PPG signal can also be detected, as desired, such as but not limited to the minimum amplitude of the PPG signal, the maximum upward slope of the PPG signal, the maximum amplitude of the PPG signal, the maximum downward slope of the PPG signal prior to the dicrotic notch, the dicrotic notch of the PPG signal and the maximum downward slope of the PPG signal following the dicrotic notch.

For much of above description, it has been assumed that the plethysmography sensor used to produce a plethysmography signal is a PPG sensor. Thus, the plethysmography signal has often been referred to as a PPG signal. However, it should be noted that other types of plethysmography sensors can alternatively be used. Thus, embodiments of the present invention should not be limited to use with PPG sensors and PPG signals. For example, in specific embodiments, the arterial plethysmography signal can be produced using non-radiant methods and devices, including, but not limited to mechanical strain, electrical impedance, or pressure. More specifically, rather than using a PPG sensor that includes a light source and detector, the implanted plethysmography sensor can include a strain gauge, a linear displacement sensor, or an ultrasound transducer, each of which is known in the art. Alternatively, an impedance plethysmography sensor (IPG), which is also known in the art, can be used. The impedance measuring circuit 213 shown in FIG. 2 can provide or be part of an IPG sensor. Details of exemplary implantable sensors that produce an impedance plethysmography signals are disclosed, e.g., in U.S. Pat. Nos. 4,674,518, 4,686,987 and 5,334,222 (all to Salo or Salo et al.), which are incorporated herein by reference.

Figure 2:
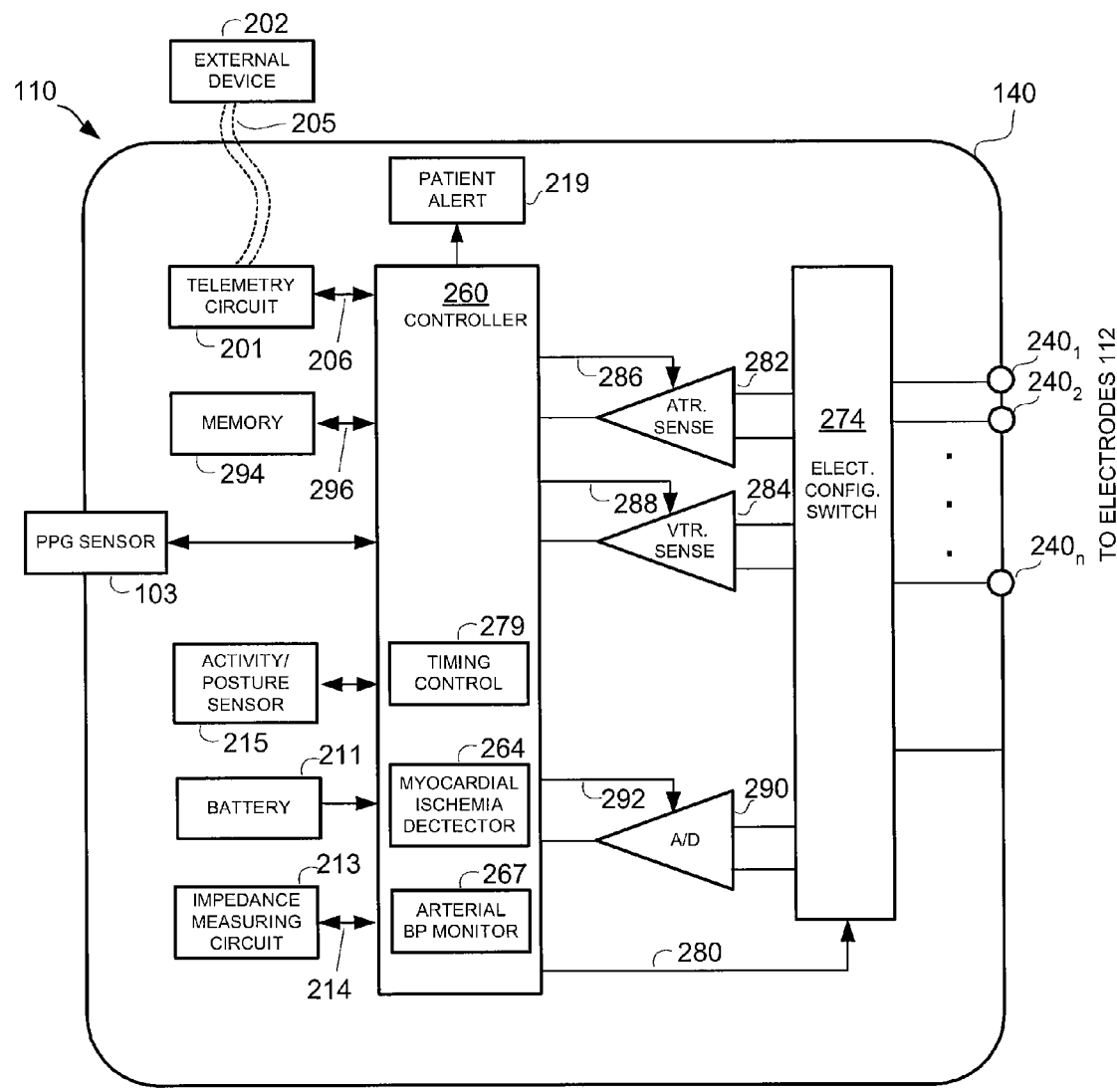
FIG. 2 is a simplified block diagram that illustrates possible components of the implantable devices shown in FIGS. 1A-1F.

FIG. 2 will now be used to provide some exemplary details of components of the implantable devices 110. Referring now to FIG. 2, each of the above implantable devices 110, and alternative versions thereof, can include a microcontroller 260. As is well known in the art, the microcontroller 260 typically includes a microprocessor, or equivalent control circuitry or state machine circuitry, and can further include RAM or ROM memory, logic and timing circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with determining values of arterial blood pressure and detecting episodes of myocardial ischemia.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). These are just a few examples, which are not meant to be limiting.

The housing 140, shown schematically in FIG. 2, is often referred to as the "can", "case" or "case electrode" and may be programmably selected to act as one of the subQ electrodes. The housing 140 can further include a connector (not shown) having a plurality of terminals 240 which can be connected to the electrodes 112.

The microcontroller 260 can further include timing control circuitry 279 which can be used to control sensing parameters (e.g., detection windows, alert intervals, marker channel timing, etc.), which are well known in the art.

The switch bank 274 includes a plurality of switches for connecting the desired electrodes 112 to the appropriate I/O circuits, thereby providing electrode programmability. Accordingly, the switch 274, in response to a control signal 280 from the microcontroller 260, determines which electrodes are being used to produce an ECG, by selectively closing the appropriate combination of switches (not shown) as is known in the art.

Atrial sensing circuits 282 and ventricular sensing circuits 284 may also be selectively coupled to the various electrodes for obtaining an ECG. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

FIG. 2 also shows the PPG sensor 103, which can be within, integral with or attached to the housing 140, or remote from the housing 140, as was described in detail above.

Figure 4A:
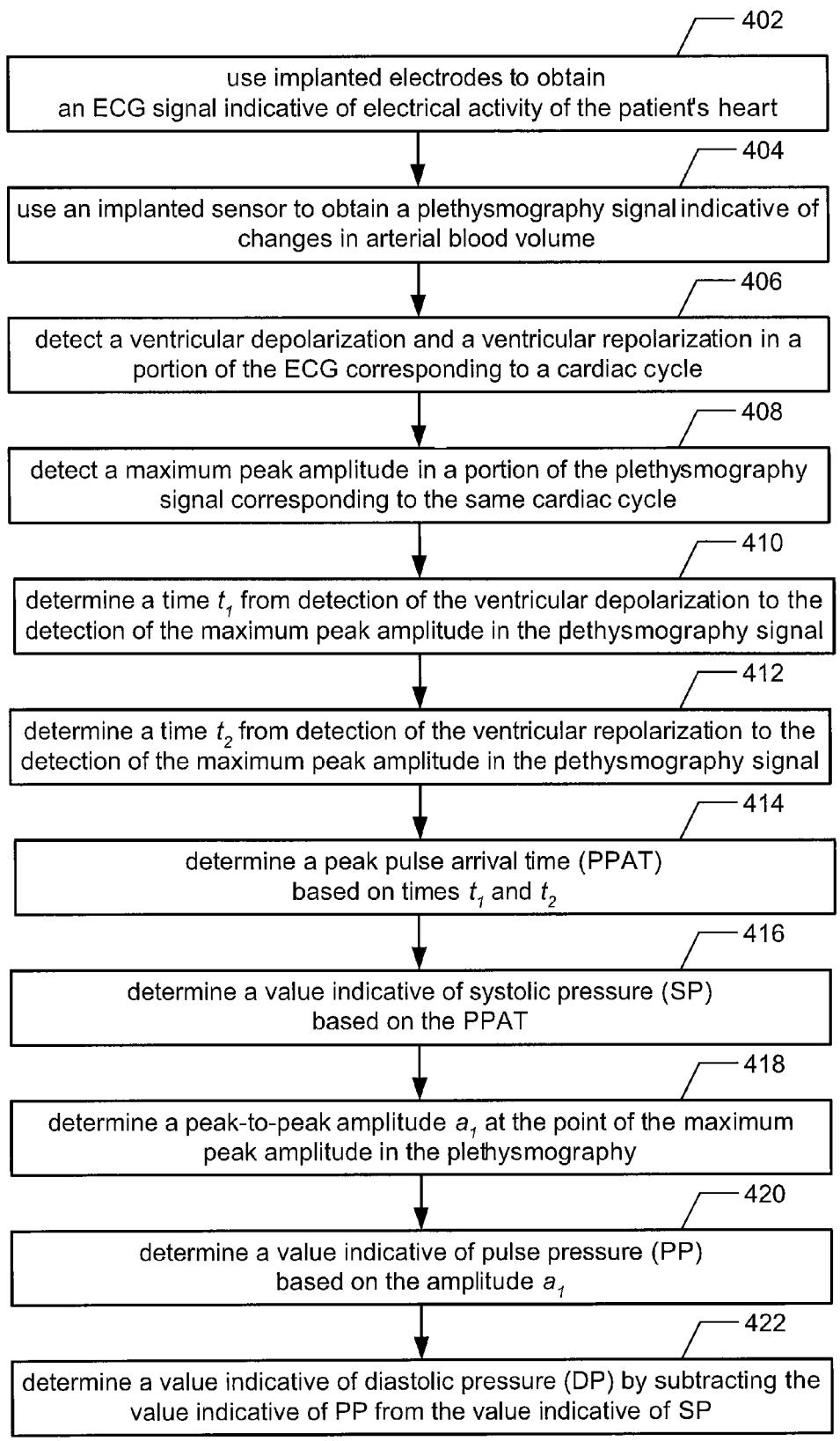
FIGS. 4A and 4B are high level flow diagrams that are used to explain techniques for monitoring arterial blood pressure that can be performed using the standalone blood pressure monitoring devices, according to embodiments of the present invention.
Figure 4B:
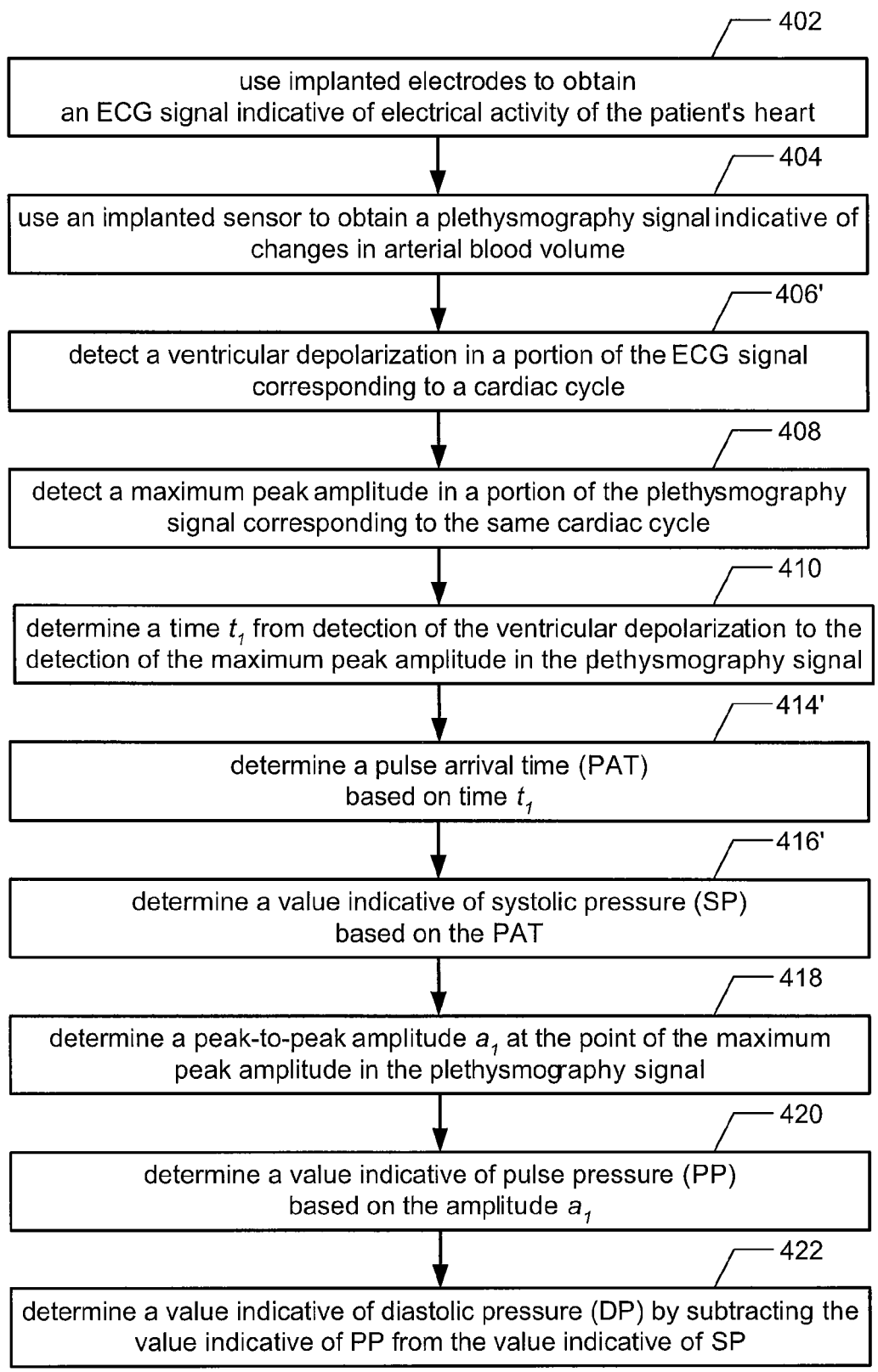

In accordance with embodiments of the present invention, the implantable device 110 includes an arterial blood pressure monitor 267, which can determine values indicative of systolic pressure (SP), diastolic pressure (DP), pulse pressure (PP) and/or mean arterial pressure (MP), as well as changes in each, using the techniques described below with reference to FIGS. 3, 4A and 4B. The arterial blood pressure monitor can have a portion that detects features of the SubQ ECG, and another portion that detects features of the plethysmography signal, and a further portion that determines the value(s) indicative of the patient's arterial blood volume, or all or some such portions can be combined. The arterial blood pressure monitor 467 can be implemented within the microcontroller 460, as shown in FIG. 4, and can the be implemented by software, firmware, or combinations thereof. It is also possible that all, or portions, of the monitor 467 to be implemented using hardware. Further, it is also possible that all, or portions, of the monitor 467 to be implemented separate from the microcontroller 460.

To detect posture and/or activity, an implantable device 110 can include a sensor 215, which can detect a patient's posture and/or level of activity. The sensor can be, e.g., a DC-coupled 3-dimensional accelerometer as described in U.S. Pat. No. 6,658,292 (Kroll et al), a multi-axis DC accelerometer as described in U.S. Pat. No. 6,466,821 (Pianca et al), or an external field sensor as described in U.S. Pat. No. 6,625,493 (Kroll et al), each of which are incorporated herein by reference. Such sensors are able to distinguish among different static positions. In addition, since the sensors can detect motion, they can be used to distinguish between a static vertical position, such as sitting, and a standing position, which due to the dynamics of balance is associated with subtle motion that is not present while sitting. In this way an implantable system, using one of the above mentioned sensors or other sensing modality, can detect a change in body position (i.e., posture), which can be used as a trigger to perform specific methods of the present invention described below.

In accordance with embodiments of the present invention, the implantable device 110 also includes an ischemia detector 264, which can detect ischemic events based, e.g., on ST-segment shift analysis. The ischemia detector 264 can be implemented within the microcontroller 260, as shown in FIG. 2. Thus, this detector 464 can be implemented by software, firmware, or combinations thereof. It is also possible that all, or portions, of the ischemia detector 264 can be implemented using hardware. Further, it is also possible that all, or portions, of the ischemia detector 264 can be implemented separate from the microcontroller 260.

The ischemia detector 264 can monitor sensed cardiac signals in order to detect and record timing and duration information relating to myocardial ischemic episodes. Ischemia detector 264 may also trigger a patient or physician alert in response to detecting a myocardial ischemic event. For example, a patient alert 219, which produces a vibratory or auditory alert, may be triggered. Additionally, or alternatively, the implantable device can also monitor for episodes and degrees of myocardial ischemia, and there could be a cross-correlation of arterial blood pressure values with degrees of ischemia (as well as with levels of activity and/or posture). This can be useful, e.g., for determining the seriousness associated with ischemic episodes. For example, severe ischemia associated with a drop in arterial blood pressure at low levels of activity is more serious than a mild degree of ischemia with no drop in blood pressure at high levels of activity.

There are many documented techniques for detecting episodes of myocardial ischemia. Many of these techniques perform ST-segment shift analysis to determine if there is a deviation of the ST-segment from a baseline (e.g., a PQ segment baseline), and detect myocardial ischemic events when the deviation is beyond a threshold. Other techniques are also possible. In specific embodiments, the implanted device can detect myocardial ischemic events based on the ECG signals obtained by the device 110. For example, known techniques can be used that perform ST-segment shift analysis to determine if there is a deviation of the ST-segment from a baseline (e.g., a PQ segment baseline), and detect myocardial ischemic events when the deviation is beyond a threshold. Other techniques are also possible. The precise technique used to detect episodes of myocardial ischemia are not important to the present invention. Rather, what is important is that episodes of myocardial ischemia can be detected, so that such information can be correlated with arterial blood pressure information, and preferably information showing such correlations can be stored. For example, the implantable device can store, in memory, arterial blood pressure data (obtained using embodiments of the present invention) corresponding to the period immediately prior to, during and subsequent to a detected myocardial ischemic episode. The implantable device can also store data that identifies the ST-segment level during various portions of an episode (e.g., at onset of the ischemia, the peak of the ischemia and the termination of the ischemia), the time of the ischemic episodes (at onset, at peak and/or at termination), the duration of the episode, as well as any other type of information that a physician may deem useful. U.S. Pat. Nos. 6,112,116, 6,272,379 and 6,609,023 (all to Fischell et al.), which are incorporated herein by reference, provide exemplary additional details of the types of data that can be stored in response to the detection of a myocardial ischemic episode, and how such data can be efficiently and effectively stored. Additionally, corresponding arterial blood pressure information, such as values indicative of SP, DP and/or MAP can also be stored. This would enable the implantable device, or an external system and/or physician (which receives the information from the implantable system) to analyze how such conditions are inter-related.

Still referring to FIG. 2, cardiac signals are also applied to the inputs of an analog-to-digital (A/D) data acquisition system 290. The data acquisition system 290 is configured to acquire ECG signals, convert the raw analog data into a digital signal, and store the digital signals for later processing and/or telemetric transmission to an external device 202. The data acquisition system 290 can be selectively coupled to the various electrodes 112 through the switch 274 to sample cardiac signals across any pair of desired electrodes. In specific embodiments, the data acquisition system 290 may be used to acquire ECG signals for use in monitoring arterial blood pressure using techniques described below, and possibly for the analysis of changes in the ST-segment for detecting myocardial ischemia.

The microcontroller 260 is further coupled to the memory 294 by a suitable data/address bus 296, wherein the programmable operating parameters used by the microcontroller 260 are stored and modified, as required, in order to customize the operation of the implantable device 210 to suit the needs of a particular patient. The memory 294 can also store arterial blood pressure data.

The operating parameters of the implantable device 110 may be non-invasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows ECG data, arterial blood pressure data and status information relating to the operation of the device 210 (as contained in the microcontroller 260 or memory 294) to be sent to the external device 202 through an established communication link 204.

For examples of telemetry devices, see U.S. Pat. No. 4,809, 697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 110 additionally includes a battery 211 which provides operating power to all of the circuits shown in FIG. 2.

The implantable device 110 can also include a magnet detection circuitry (not shown), coupled to the microcontroller 260. It is the purpose of the magnet detection circuitry to detect when a magnet is placed over the implantable device 110, which magnet may be used by a clinician to perform various test functions of the implantable device 110 and/or to signal the microcontroller 260 that the external programmer 202 is in place to receive or transmit data to the microcontroller 260 through the telemetry circuits 201. The magnet may also be used by a patient to indicate for the implantable device to record signals or perform a blood pressure measurement.]

As further shown in FIG. 2, the device 110 is also shown as having an impedance measuring circuit 213 which is enabled by the microcontroller 260 via a control signal 214. The known uses for an impedance measuring circuit 213 include, but are not limited to, lead impedance surveillance. The impedance measuring circuit 213 is advantageously coupled to the switch 274 so that any desired electrode may be used. The impedance measuring circuit 213 may also be used to obtain impedance plethysmography (IPG) signals.

Referring to FIG. 3, the signal waveforms therein are used to show the relative timing of electrical and mechanical cardiac events that occur during a cardiac cycle. The upper graph includes an aortic pressure waveform 302, a left atrial pressure waveform 304 and a left ventricular pressure waveform 306. The middle graph includes a subQ electrocardiogram (ECG) waveform 308, which is shown as including a P wave, a QRS complex (including Q, R and S waves) and a T wave. The P wave is caused by depolarization of the atria. This is followed by atrial contraction, which is indicated by a slight rise in the atrial pressure (seen in waveform 304) contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. Ventricular repolarization occurs thereafter, as indicated by the T wave and this is associated with the onset of ventricular relaxation in which forward flow stops from the ventricles into the aorta and pulmonary arteries, the pressure in the ventricles falls below that in the atria at which time the mitral and tricuspid valves open to begin to passively fill the ventricle during diastole with forward flow from the atria to the ventricles. Also shown in FIG. 3, in the bottom graph, is a photoplethysmography (PPG) signal 310, which will be described in additional detail below.

In accordance with specific embodiments of the present invention, a subQ ECG signal (e.g., like 308) is obtained using implanted subQ electrodes 112. Additionally, a plethysmography signal (e.g., a PPG signal like 310), is obtained from an implanted sensor. In accordance with specific embodiments of the present invention, by detecting the timing and amplitude of certain features of such signals, various arterial blood pressure measurements can be obtained, including systolic pressure (SP), diastolic pressure (DP), pulse pressure (PP) and/or mean arterial pressure (MAP). As mentioned above, the systolic pressure (SP) is the peak pressure in the arteries, which occurs near the beginning of a cardiac cycle. The DP is the lowest pressure in the arteries, which occurs at the end of the resting phase of the arterial circulation. This corresponds to the end of the filling[PAL1] phase of the cardiac cycle with respect to ventricular function. The PP is the difference between the systolic and diastolic pressures. The MAP is a weighted average of pressure throughout the cardiac cycle.

Because implanted electrodes and an implanted sensor are used to obtain the various arterial pressure measurements, a patient's arterial blood pressure can be monitored on a chronic basis. Thus, arterial blood pressure can be tracked to monitor a patient's worsening (or improving) cardiac disease state, and to trigger alerts (e.g., in response to which a patient may take blood pressure medications). Additionally, arterial blood pressure measurements can be used as a measure of hemodynamic function.

Embodiments of the present invention use the concept of pulse arrival time, also known as pulse transmit time, or pulse wave velocity to monitor arterial blood pressure. However, embodiments of the present invention differ from prior art non-implanted systems that rely on pulse arrival time. Accordingly, most such prior are systems are not practical for chronic use.

The inventors of the present invention are aware of one prior art reference, i.e., U.S. Pat. No. 4,425,920 (Bourland et al.), that does suggest an implantable system for monitoring arterial blood pressure using the concept of pulse transmit time. However, the system of the '920 patent requires that two sets of electrodes be positioned adjacent a same artery at two sites, and thus, requires very precise and potentially difficult implantation of its system. In contrast, the implantable systems of many of the embodiments of the present invention can be implanted subcutaneously in a quick and minimally invasive manner.

Additionally, many embodiments of the present invention use a novel measure, referred to below as peak pulse arrival time (PPAT), which is believed to provide for improved measures of arterial blood pressure. Referring to FIG. 3, it can be seen that a time of the peak arterial blood pressure, represented by dashed line 312, occurs at a time between ventricular depolarization (as represented by the QRS complex) and ventricular repolarization (as represented by the T wave). More specifically, it can be seen that the peak occurs generally halfway between the QRS complex and the T wave. PPAT is determined, taking this into account.

As can also be seen from FIG. 3, the peak in the PPG signal 103 occurs at a time after the peak in the arterial blood pressure (as shown in the upper graph). This is because the peak in the PPG signal 103 is indicative of the peak wave in arterial blood pressure generated by the patient's heart, as detected by a PPG sensor 103 located a distance from the patient's heart. Presuming the PPG sensor 103 is implanted in the pectoral region of the patient (which is an option, but not necessary), the time that it takes a peak pulse wave (as detected from subQ ECG electrodes) to travel from the patient's heart to the PPG sensor 103 can be, e.g., on the order of 10-100 msec, depending on the location of the subQ electrodes 112 (used to obtain the subQ ECG) and the location of the PPG sensor. The peak pulse wave is initially detectable from a subQ ECG obtained using implanted subcutaneous electrodes. The time at which the peak wave reaches the implanted PPG sensor is detectable from a PPG signal produced by the implanted PPG sensor. Accordingly, the amount of time it takes a peak pulse wave to travel from the patient's heart to the PPG sensor 103 can be determined. Such information is used to determine values of arterial blood pressure. It is also possible, and within the scope of the present invention, that the time it takes a peak pulse to travel from the patient's heart to the PPG sensor can be outside the 10-100 msec range mentioned above.

Techniques for monitoring blood pressure using the devices of FIGS. 1A-1F will be summarized with reference to the high level flow diagrams of FIGS. 4A and 4B. In the flow diagrams, the various algorithmic steps are summarized in individual 'blocks'. Such blocks describe specific actions or decisions that are made or carried out as the algorithm proceeds. Where a microcontroller (or equivalent) is employed, the flow diagram presented herein provides the basis for a 'control program' that may be used by such a microcontroller (or equivalent) to effectuate the desired control of the implantable system. Those skilled in the art may readily write such a control program based on the flow diagram and other descriptions presented herein.

Referring to FIG. 4A, at step 402, implanted electrodes (e.g., 112) are used to obtain a subQ ECG signal indicative of electrical activity of the patient's heart. A portion of an exemplary subQ ECG signal indicative of electrical activity of the patient's heart is shown at 308 in FIG. 3.

At step 404, an implanted sensor (e.g., 103) is used to obtain a plethysmography signal indicative of changes in arterial blood volume. In specific embodiments, the signal can be a photoplethysmography (PPG) signal. An exemplary portion of a PPG signal is shown at 310 in FIG. 3. Alternatively, the signal can be an impedance plethysmography signal (IPG). In still other embodiments, the plethysmography signal can be a signal output by a sensor including a piezo-electric diaphragm. Alternative sensors that can be used to produce the plethysmography signal, include, but are not limited to, a close range microphone, a sensor including a small mass on the end of a piezo bending beam with the mass located on the surface of a small artery, a transmission mode infrared motion sensor sensing across the surface of a small artery, or a MEMS accelerometer located on the surface of a small artery. Such alternative sensors can be located, e.g., on the tip of a short lead connected to a device that is subcutaneously implanted. The implanted sensor is preferably extravascular, and preferably a sufficient distance from the patient's heart such that meaningful changes in the amount of time it takes a pulse wave originating in the heart to reach the implanted sensor can be detected, thereby enabling changes in arterial blood pressure to be detected. For example, it is preferred that the implanted sensor (used to obtain the signal indicative of changes in arterial blood volume) is at least 10 mm from the patient's aortic root. Such a sensor can be implanted, e.g., in the pectoral region of a patient. An alternative location for implantation of the sensor includes, but is not limited to, the patient's abdominal region.

At step 406, a ventricular depolarization and a ventricular repolarization are detected in a portion of the subQ ECG signal corresponding to a cardiac cycle. A QRS complex, such as the one shown in signal 308 of FIG. 3, is indicative of ventricular depolarization. Ventricular depolarization can be detected, e.g., by detected the Q wave of the QRS complex, the R wave of the QRS complex, and/or the S wave of the QRS complex. However, since the R wave is the easiest to detect, due to its relatively large magnitude, it is practical for ventricular depolarization to be detected by detecting the R wave. Accordingly, any known or future developed technique for detecting an R wave (e.g., by peak detection or threshold crossing) can be used to detect ventricular depolarization. Exemplary techniques for detecting R waves are disclosed in U.S. patent application Ser. No. 10/998,026, entitled "Systems and Methods for Detection of VT and VF from Remote Sensing Electrodes" (Nabutovsky et al.), filed Nov. 24, 2004, which is incorporated herein by reference. Alternatively, known or future developed techniques for detecting the Q, R and/or S waves can be used to detect ventricular depolarization.

A T wave, such as the one shown in signal 308 in FIG. 3, is indicative of ventricular repolarization. Accordingly, any known or future developed technique for detecting a T wave can be used to detect ventricular repolarization. Some exemplary techniques for detecting T waves are disclosed in U.S. patent application Ser. No. 10/979,833, entitled "Systems and Methods for Automatically Setting Refractory and Blanking Periods," (Snell and Bharmi) filed Nov. 1, 2004, which is incorporated herein by reference. Some additional exemplary techniques for detecting T waves are disclosed in U.S. Pat. No. 5,782,887 (van Krieken et al) and U.S. Pat. No. 6,836,682 (Van Dam), which are incorporated herein by reference. Use of alternative techniques for detecting T waves are within are also within the scope of the present invention."

At step 408, a maximum peak amplitude is detected in a portion of the plethysmography signal corresponding to the same cardiac cycle referred to in step 406. For the following discussion, it will be assumed that the plethysmography signal is a PPG signal. A peak detection circuit, a peak detection algorithm or the like, can be used to detect the peak amplitude of a PPG signal (or other plethysmography signal), as is well known in the art. As will be discussed below with reference to step 418, the peak-to-peak amplitude $a_1$ at this point in the plethysmography signal (i.e., at the point where the PPG signal amplitude is maximum) should also be determined. Thus, it would be practical to perform steps 408 and 418 at generally the same time.

At step 410, there is a determination of a time $t_1$ from detection of the ventricular depolarization to the detection of the maximum peak amplitude in the plethysmography signal. In other words, time $t_1$ is the time from the QRS complex, or a component thereof (e.g., Q wave, R wave or S wave) to the peak of the plethysmography signal (e.g., the peak of the PPG signal). An exemplary time $t_1$ is shown in FIG. 3.

Ventricular depolarization occurs at the beginning of systole, which substantially coincides with the end of diastole (ED in FIG. 3). The maximum peak amplitude of the plethysmography signal occurs when a mechanical pulse resulting from the ventricular depolarization is detected by the plethysmography sensor, which is a distance from a location in the patient's heart where the pulse originated. For example, the plethysmography sensor (e.g., a PPG sensor) can be implanted in the pectoral region, e.g., attached directly to (or by a lead to) the housing 140 of the implanted device 110, as was described above. According, the time $t_1$ is indicative of the time from the beginning of systole (or end of diastole) to the peak in the mechanical pulse detected by an implanted sensor.

At step 412, there is a determination of a time $t_2$ from the detection of the ventricular repolarization to the detection of the maximum peak amplitude in the plethysmography signal. As just explained, the maximum peak amplitude of the plethysmography signal occurs when a mechanical pulse resulting from the ventricular depolarization is detected by the plethysmography sensor, which is a distance from the location in the patient's heart where the pulse originated. As explained above, the T wave in the subQ ECG signal is indicative of ventricular repolarization. Accordingly, the time $t_2$ can be determined by determining the time from the T wave in the SubQ ECG signal to the time of the peak amplitude in the plethysmography signal (e.g., a PPG signal). Ventricular repolarization occurs at the end of systole. Accordingly, the time $t_2$ is indicative of the time from the end of systole to the peak in the mechanical pulse detected by an implanted sensor.

At step 414, a peak pulse arrival time (PPAT) is determined based on times $t_1$ and $t_2$. The diastolic pressure (DP), which is the lowest arterial blood pressure, occurs at the end of diastole (ED in FIG. 3), which substantially coincides with the beginning of systole. The systolic pressure (SP), which is the peak arterial blood pressure, occurs during systole, at a time between the beginning of systole and the end of systole (ES in FIG. 3). In specific embodiments it is assumed that systole is substantially symmetric, and thus that the peak in systole occurs substantially between the beginning and end of systole. Accordingly, in specific embodiments, PPAT is the mean of times $t_1$ and $t_2$. In other words, PPAT can be determined using the equation PPAT=$(t_1+t_2)/2$. In still other embodiments, slight variations on this formula can be used. For example, it may be determined that the value 2 in the denominator of the PPAT equation should be replaced with 1.8 or 2.2, or the like, if it is determined that the peak in systole is slightly asymmetric.

At step 416, a value indicative of systolic pressure (SP) is determined based on the PPAT. PPAT is inversely related to SP, in that the greater the PPAT the lower the SP, and the lower the PPAT the greater the SP. In a simplest embodiment, SP≈1/PPAT. However, it would be preferred to use a patient specific correlation factor (e.g., a constant K) when determining SP. In other words, in specific embodiments, SP=K/PPAT, where K is determined during a calibration procedure. More specifically, an actual value of SP is determined using any known accurate acute technique, and a value of PPAT is measured in the manner described above using an implanted system. This will result in K being the only unknown factor in the equation, and thus, K would be easily calculable (e.g., by an external programmer, or the like). The patient could also be asked to exercise, or could be appropriately paced, to change the patient's SP, to thereby check the accuracy of K over a range of SPs and PPATs. If appropriate, K can be adjusted so that K is accurate over a range of systolic pressures. Presuming PPAT is measured in msec, the units of K can be mmHg·msec, so that when K is multiplied by 1/PPAT, the resulting SP has units of mmHg. Use of look up tables and interpolation are also within the scope of the present invention.

In summary, at step 414, SP can be determined based on PPAT using an equation (e.g., SP=K/PPAT), or using a simple look-up table. An alternative equation could be SP=K/PPAT+β. In a similar manner as just described, β can be determined during a calibration procedure. Other formulas are also possible, and could be derived by determining actual values of the SP for various different values of PPAT, and are within the scope of the present invention.

An exemplary calibration procedure (performed at implant and/or thereafter) will now be explained. During the calibration procedure, actual measures of arterial blood pressure, including SP and DP, are measured along with values of PPAT (and peak-to-peak amplitude $a_1$, as will be discussed below). The actual measure of the patient's SP and DP can be obtained, e.g., using a non-invasive auscultatory or oscillometric techniques, or an invasive intravascular cannula method, or any other acute technique. For a more specific example, actual arterial pressure measurements (SP and DP) can be measured using a high fidelity micronometer-tipped pressure catheter (e.g., model 4F, SPC-120, available from Millar Instruments, Texas), which is placed in the ascending aorta via a carotid arteriotomy. Other techniques are also possible, and within the scope of the present invention.

Still referring to FIG. 4A, at step 418, a peak-to-peak amplitude $a_1$ in the plethysmography signal (e.g., a PPG signal) is determined, at the point of the peak amplitude in the plethysmography signal (detected at step 408). For example, one or more peak detection circuit can be used to detect the peak-to-peak amplitude $a_1$. Alternatively, software, hardware and/or firmware can be used to detect the peak-to-peak amplitude $a_1$ based on sample data points of the PPG signal, e.g., by determining a difference between maximum and minimum sample values of a PPG signal for each cardiac cycle, or a similar algorithm. An exemplary peak-to-peak amplitude $a_1$ is shown in FIG. 3. As mentioned above, it would be practical to perform steps 408 and 418 at generally the same time.

Steps 420 and 422 will now be discussed together. At step 420, a value indicative of pulse pressure (PP) is determined based on the amplitude $a_1$. At step 422, a value indicative of diastolic pressure (DP) is determined by subtracting the value indicative of PP from the value indicative of SP (i.e., DP=SP−PP). The value indicative of PP is mainly determined so that the value of DP can be determined. Accordingly, steps 420 and 422 together can be collectively thought of as determining a value of DP based on the value of SP (determined at step 416) and the value of $a_1$ (determined at step 418).

Peak-to-peak amplitude $a_1$ is directly related to the PP, in that the greater $a_1$ the greater the PP, and the lower the $a_1$ the lower the PP. In a simplest embodiment, PP≈$a_1$. However, it would be preferred to use a patient specific correlation factor (e.g., a constant M) when determining PP. In other words, in specific embodiments, PP=M·$a_1$, or possibly PP=M·$a_1$+σ, where M (and possibly also σ) can be determined during a calibration procedure, as will be described below.

During calibration, while actual values of SP are being determined for various PPAT values, actual values of DP can also be determined for various values of $a_1$. This will enable the patient specific correlation factor M (and possibly also σ) to be determined during the calibration procedure. For example, by combining PP=M·$a_1$ with DP=SP−PP, a resulting equation is DP=SP−(M·$a_1$). Since actual values of DP and SP can be obtained during calibration (at implant and/or thereafter), and values of $a_1$ can be measured during calibration, the patient specific correlation factor M (and possibly also σ) can be easily determined. Other formulas are also possible, and could be derived by determining actual values of the DP for various different values of $a_1$. After implant, in similar manners as were discussed above with reference to step 418, an algorithm or look-up table can be used to calculate PP based on $a_1$ at step 420.

Once SP and DP are determined (at steps 416 and 422), mean arterial pressure (MAP) can also be determined. For example, the equation MAP=⅓ SP+⅔ DP can be used. Alternatively, the equation MAP=(SP+DP)/2 can be used. Use of other equations is also within the scope of the present invention.

In step 414 described above, the peak pulse arrival time (PPAT) is determined based on times $t_1$ and $t_2$. It is believed that increased accuracy can be obtained by using PPAT in step 416 to determine the systolic pressure (SP), as compared to using a more simple pulse arrival time (PAT). Nevertheless, in alternative embodiments, described with reference to FIG. 4B, at step 414' a pulse arrival time (PAT) is determined based on $t_1$ (but not $t_2$), and at step 416' the systolic pressure (SP) is determined based on PAT. In a simplest embodiment, SP≈1/PAT. Alternatively, SP=K/PAT, or SP=K/PAT+β. In a similar manner as was described above, K (and possibly β) can be determined during a calibration procedure. Other formulas are also possible, and could be derived by determining actual values of the SP for various different values of PAT. Since time $t_2$ is not used to determine PAT, at step 406' ventricular repolarization need not be detected to determine PAT (however, T waves may be detected for other, unrelated reasons). Additionally, step 412 need not be performed, and is thus not shown in FIG. 4B.

In accordance with specific embodiments of the present invention, arterial blood pressure information such as the value indicative of SP (obtained at step 416), the value indicative of DP (obtained at step 422), the value of MAP determined based on SP and DP, and potentially other information is stored within memory of the implantable system for later analysis within the device and/or for later transmission to an external device. Such an external device (e.g., an external programmer or external monitor) can then be used to analyze such data.

Embodiments of the present invention are not limited to the exact order and/or boundaries of the steps shown in FIGS. 4A and 4B. In fact, many of the steps can be performed in a different order than shown, and many steps can be combined, or separated into multiple steps. All such variations are encompassed by the present invention. For example, steps 408 and 418 can be combined into a single step, or step 418 can immediately follow step 408. For another example, step 406 can be separated into two steps, one where ventricular depolarization is detected, and another where ventricular repolarization is detected. The only time order is important is where a step acts on the results of a previous step. For example, PPAT can not be determined at step 416 until times $t_1$ and $t_2$ are determined at steps 412 and 414. However, steps 412 and 414 can be combined, or their order can be swapped.

In accordance with specific embodiments of the present invention, an alarm can be triggered based on comparisons of the values indicative of SP, the values indicative of DP, the changes in SP and/or the changes in DP to corresponding thresholds. Such an alarm can be part of an implanted system. Alternatively, an implanted system can trigger a non-implanted alarm of a non-implanted system. In still other embodiments, where arterial pulse pressure information is transmitted (e.g., via telemetry) to an external device, a non-implanted alarm can be triggered based on comparisons of the values indicative of SP, the values indicative of DP, the changes in SP and/or the changes in DP, received by the non-implanted device, to corresponding thresholds. Values indicative of SP and DP can be used to determine values of indicative of MAP, and corresponding MAP thresholds can be used to trigger alarms or the like.

In accordance with specific embodiments of the present invention, the method described with reference to FIG. 4A or 4B can be repeated from time-to-time, to thereby track changes in SP, DP and/or MAP. For example, steps 402-422 can be performed periodically (e.g., once a minute, hour, day, week, or the like). The values indicative of SP, DP and/or MAP can be compared in real time to corresponding thresholds. Alternatively, or additionally, values indicative of SP, DP and/or MAP can be stored in memory of the implanted system. Such stored values can be analyzed by the implanted system and/or transmitted (e.g., via telemetry) to an external system (e.g., external programmer and external monitor) and analyzed by the external system. Use of various thresholds can be used to trigger alarms and/or therapy, as will be described below.

Depending on the frequency, periodic monitoring of arterial blood pressure may be costly in terms of energy, memory and/or processing resources. Accordingly, it may be more efficient to trigger the performance of certain steps upon detection of an event, such as a specific activity, or lack thereof, and/or a specific posture of the patient. For example, an activity sensor and/or posture sensor (e.g., sensor 215) can be used to trigger the performance of steps 402-422. For example, steps 402-422 can be triggered when it is detected that a patient is inactive and lying down. Additionally, or alternatively, steps 402-422 can be triggered when a patient is upright and walking. In still other embodiments, steps 402-422 can be triggered to occur, at specific intervals following a patient changing their posture (e.g., assuming an upright posture) and/or activity level. For example, following a triggering event, values of arterial blood pressure can be determined once a minute for 10 minutes, or at 1 minute, 2 minutes, 5 minutes and 10 minutes after the triggering event. Of course, other variations are also possible, and within the scope of the present invention. It may also be that one or more specific step, such as step 402, is performed substantially continually (e.g., because the signals obtained at step 402 are also used for pacing, arrhythmia detection, and the like), but other steps (e.g., steps 404-422) are only performed in response to a triggering event, such as those discussed above.

It is normal for there to be a normal circadian variation in arterial blood pressure values, including SP, DP and MAP values. For example, a drop in such values when a patient is sleeping, at rest and/or supine is normal. However, a drop in such values when a patient is active, or upright, or within a short period of a patient assuming an upright posture, is abnormal. Implanted activity and/or posture sensors (e.g., sensor 215) can thus be used to assist in defining when an alarm or the like should be triggered. For example, a posture sensor can be used to trigger the monitoring of arterial blood pressure values when a patient assumes an upright posture. In this manner, such monitoring can be used to determine whether a drop in blood pressure within a specific amount of time (e.g., 10 minutes), following the patient assuming of an upright position, exceeds a specified threshold. Such a threshold can be, e.g., an absolute value or a percentage. In specific embodiments, the SP, DP and/or MAP thresholds to which determined SP, DP and/or MAP values are compared can be based on the activity and/or posture of the patient.

Where at least some of steps 402-422 are triggered in response to detection of various different activity and/or posture states, information about the patient's activity and/or posture can also be stored along with the arterial blood pressure information, so that such information can be correlated. In other words, there could be a cross-correlation of arterial blood pressure values with levels of activity and/or posture.

Accordingly, embodiments of the present invention can be used to determine, or assist with the determination of, whether there is a correlation between levels of arterial blood pressure, levels of activity and/or posture, and myocardial ischemic episodes experienced by a patient. Such information will enable a medical practitioner to analyze whether ischemic episodes that the patient experienced may have precipitated changes in arterial blood pressure, posture and/or activity.

In accordance with specific embodiments of the present invention, measures of arterial blood pressure, including values indicative of SP, DP, PP and/or MAP can be stored so that a physician or clinician can upload such measurements when visiting the physician or clinician.

More generally, measures of arterial blood pressure, obtained in accordance with embodiments of the present invention can be used to assess the hemodynamic status of a patient. This can include tracking a patient's cardiac disease state, including but not limited to, heart failure. For example, increases in measures of arterial blood pressure over time can be interpreted as a worsening of a heart failure condition.

Alternative embodiments of the present invention are directed to non-implantable monitoring devices to monitor a patient's arterial blood pressure. In certain embodiments, such a device can be configured to be worn against a patient's skin. The device can resemble the devices described above (e.g., with reference to FIG. 1A or 1B), but the device would include surface electrodes worn against the patient's skin (instead of being implanted) so that a surface electrocardiogram (surface ECG) that is indicative of electrical activity of the patient's heart can be obtained. An arterial blood pressure monitor can be located within a device housing, and can be configured to perform similar functions as arterial blood pressure monitor 267. In certain embodiments, the surface ECG electrodes can be attached to the housing, e.g., substantially flush with and/or adjacent to the housing. In such embodiments, the housing can be worn against a patient's skin. In other embodiments, the surface ECG electrodes can be remote from the housing and configured to be mounted on a patient's skin, e.g., outside of a patient's rib cage.

In some embodiments the plethysmography sensor (e.g., PPG sensor) of the non-implantable monitoring device can be within, integral with or attached to the housing (e.g., a light source and a light detector can be within, integral with or attached to the housing). In such embodiments, the light source and detector can face the patients skin that is adjacent the housing. Alternatively, optical fibers can be used to transmit light produced by the light source to a portion of a patient's body that is remote from the housing, and can provide a portion of the transmitted light reflected from and/or transmitted through the portion of the patient's body to the light detector. In still another embodiments, the PPG sensor can includes a light source and a light detector that are located within, integral with or attached to the lead that extends from the housing to thereby enable the light source and light detector to be placed adjacent a portion of the patient's body (e.g., a finger, earlobe, etc) that is remote from the device housing.

As with the embodiments described above, the non-implantable monitoring device can monitor changes in the patient's arterial blood pressure using techniques similar to those described with reference to FIGS. 4A and 4B, except that the electrodes and plethysmography signal would be obtained from non implanted electrodes and a non-implanted plethysmography sensor.

Embodiments of the present invention have been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 4A and 4B. Further, it is possible to change the order of some of the steps shown in FIGS. 4A and 4B, without substantially changing the overall events and results. For another example, it is possible to change the boundaries of some of the blocks shown in FIG. 2.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. An implantable monitoring device to monitor a patient's arterial blood pressure and configured to be implanted subcutaneously, the device comprising:
   subcutaneous (SubQ) electrodes configured to obtain a subcutaneous electrocardiogram (SubQ ECG) that is indicative of electrical activity of the patient's heart;
   a plethysmography sensor configured to obtain a plethysmography signal indicative of changes in the patient's arterial blood volume; and
   an arterial blood pressure monitor configured to detect a predetermined feature of the SubQ ECG signal indicative of ventricular depolarization, detect a predetermined feature of the SubQ ECG signal indicative of ventricular repolarization, detect a predetermined feature of the plethysmography signal, and determine a time $t_1$ from the predetermined feature of the SubQ ECG indicative of ventricular depolarization to the predetermined feature of the plethysmography signal, determine a time $t_2$ from the predetermined feature of the SubQ ECG indicative of ventricular repolarization to the predetermined feature of the plethysmography signal, and determine at least one value indicative of the patient's arterial blood pressure based on the times $t_1$ and $t_2$ determined from the SubQ ECG signal and the plethysmography signal.

2. The implantable monitoring device of claim 1, wherein:
the implantable monitoring device is configured to transfer the at least one value indicative of the patient's arterial blood pressure to an non-implanted device;
the implantable monitoring device is not configured to pace the patient's heart and not configured to defibrillate the patient's heart; and
the at least one value indicative of the patient's arterial blood pressure is/are indicative of diastolic pressure (DP), systolic pressure (SP), pulse pressure (PP), mean arterial pressure (MAP), a change in DP, a change in SP, a change in PP and/or a change in MAP.

3. The implantable monitoring device of claim 1, wherein the arterial blood pressure monitor is configured to monitor changes in the patient's arterial blood pressure based on changes in the determined at least one value indicative of the patient's arterial blood pressure.

4. The implantable monitoring device of claim 1, wherein the arterial blood pressure monitor is configured to:
determine a peak pulse arrival time (PPAT) based on the times $t_1$ and $t_2$; and
determine a value indicative of systolic pressure (SP) based on the PPAT.

5. The implantable monitoring device of claim 1, further comprising:
a further sensor configured to detect activity and/or posture of the patient; and
a memory to store at least one value indicative of the patient's arterial blood pressure as determined by the arterial blood pressure monitor and a corresponding detected activity and/or posture of the patient as detected by the further sensor.

6. The implantable monitoring device of claim 1, further comprising:
a housing within which the arterial blood pressure monitor is located; and
a lead that extends from the housing;
wherein the plethysmography sensor comprises a photoplethysmography (PPG) sensor configured to obtain a photoplethysmography (PPG) signal indicative of changes in arterial blood volume; and
wherein the PPG sensor includes a light source and a light detector that are located within, integral with or attached to the lead that extends from the housing to thereby enable the light source and light detector to be placed at a location within the patient's body that is remote from a location of the housing.

7. The implantable monitoring device of claim 6, wherein the arterial blood pressure monitor is configured to detect one or more predetermined feature of the PPG selected from the group consisting of:
the minimum amplitude of the PPG signal;
the maximum upward slope of the PPG signal;
the maximum amplitude of the PPG signal;
the maximum downward slope of the PPG signal prior to the dicrotic notch;
the dicrotic notch of the PPG signal; and
the maximum downward slope of the PPG signal following the dicrotic notch.

8. The implantable monitoring device of claim 1, further comprising:
a housing within which the arterial blood pressure monitor is located; and
wherein the subQ electrodes are attached to the housing.

9. The implantable monitoring device of claim 8, wherein the subQ electrodes are substantially flush with and/or adjacent to the housing.

10. The implantable monitoring device of claim 8, further comprising:
a housing within which the arterial blood pressure monitor is located;
wherein the subQ electrodes are remote from the housing and at least some of the SubQ electrodes are configured to be mounted subcutaneously outside of a patient's rib cage.

11. The implantable monitoring device of claim 1, further comprising:
a housing within which the arterial blood pressure monitor is located;
wherein the plethysmography sensor is within, integral with or attached to the housing.

12. The implantable monitoring device of claim 11, wherein:
the plethysmography sensor comprises a photoplethysmography (PPG) sensor configured to obtain a photoplethysmography (PPG) signal indicative of changes in arterial blood volume; and
the PPG sensor comprises a light source and a light detector.

13. The implantable monitoring device of claim 12, wherein the light source and the light detector are within, integral with or attached to the housing.

14. The implantable monitoring device of claim 13, further comprising optical fibers that are configured to transmit light produced by the light source to a portion of the patient's body that is remote from the housing, and to provide a portion of the transmitted light reflected from and/or transmitted through the portion of the patient's body to the light detector.

15. The implantable monitoring device of claim 1, wherein the arterial blood pressure monitor is configured to:
determine a peak pulse arrival time (PPAT) value by determining an average of the times $t_1$ and $t_2$; and
determine at least one value indicative of the patient's arterial blood pressure based on the PPAT value.

16. The implantable monitoring device of claim 15, wherein the arterial blood pressure monitor is configured to determine a value indicative of systolic pressure (SP) based on the PPAT value.

17. The implantable monitoring device of claim 16, wherein the arterial blood pressure monitor is configured to:
determining a peak-to-peak amplitude of the plethysmography signal indicative of changes in the patient's arterial blood volume; and determine a value indicative of diastolic pressure (DP) based on the peak-to-peak amplitude and the value indicative of SP.

18. The implantable monitoring device of claim 17, wherein the arterial blood pressure monitor is configured to determine the value indicative of DP by determining a value indicative of pulse pressure (PP) based on the peak-to-peak amplitude, and determine the value indicative of DP by subtracting the value indicative of PP from the value indicative of SP.

19. The implantable monitoring device of claim 18, wherein the arterial blood pressure monitor is configured to determine a value indicative of mean arterial pressure (MAP) based on the value indicative of SP and the value indicative of DP.

20. An implantable monitoring device to monitor a patient's arterial blood pressure, the device comprising:
 subcutaneous (SubQ) electrodes configured to obtain a subcutaneous electrocardiogram (SubQ ECG) that is indicative of electrical activity of the patient's heart;
 a plethysmography sensor configured to obtain a plethysmography signal indicative of changes in the patient's arterial blood volume; and
 an arterial blood pressure monitor configured to
  detect ventricular depolarizations and ventricular repolarizations in cardiac cycles represented in the SubQ ECG signal;
  detect maximum peak amplitudes in cardiac cycles represented in the PPG signal;
  determine a time $t_1$ from a detected ventricular depolarization to a detected maximum peak amplitude in the plethysmography signal;
  determine a time $t_2$ from a detected ventricular repolarization to the detected maximum peak amplitude in the plethysmography signal;
  determine a peak pulse arrival time (PPAT) based on times $t_1$ and $t_2$; and
  determine a value indicative of systolic pressure (SP) based on the PPAT.

21. The implantable monitoring device of claim 20, wherein the arterial blood pressure monitor is configured to:
 determine a peak-to-peak amplitudes $a_1$ in the plethysmography signal; and
 determine a value indicative of diastolic pressure (DP) based on the amplitude a1 and the value indicative of SP.

22. The implantable monitoring device of claim 21, wherein the arterial blood pressure monitor is configured to:
 determine a value indicative of mean arterial pressure (MAP) based on the value indicative of SP and the value indicative of DP.

23. The implantable monitoring device of claim 20, wherein the arterial blood pressure monitor is configured to determine the PPAT by determining an average of the times $t_1$ and $t_2$.

24. An implantable monitoring device to monitor a patient's arterial blood pressure and configured to be implanted subcutaneously, the device comprising:
 a housing;
 subcutaneous (SubQ) electrodes configured to obtain a subcutaneous electrocardiogram (SubQ ECG) that is indicative of electrical activity of the patient's heart, the subQ electrodes are attached to the housing;
 a photoplethysmography (PPG) sensor configured to obtain a photoplethysmography (PPG) signal indicative of changes in the patient's arterial blood volume, the PPG sensor comprising a light source and a light detector that are within, integral with or attached to the housing;
 an arterial blood pressure monitor, within the housing, configured to
  detect a predetermined feature of the SubQ ECG signal indicative of ventricular depolarization,
  detect a predetermined feature of the SubQ ECG signal indicative of ventricular repolarization,
  detect a predetermined feature of the PPG signal, and
  determine a time $t_1$ from the predetermined feature of the SubQ ECG indicative of ventricular depolarization to the predetermined feature of the PPG signal,
  determine a time $t_2$ from the predetermined feature of the SubQ ECG indicative of ventricular repolarization to the predetermined feature of the PPG signal, and
  determine at least one value indicative of the patient's arterial blood pressure based on the times $t_1$ and $t_2$ determined from the SubQ ECG signal and PPG signal;
 wherein the implantable monitoring device is configured to transfer the at least one value indicative of the patient's arterial blood pressure to an non-implanted device;
 wherein the implantable monitoring device is not configured to pace the patient's heart and not configured to defibrillate the patient's heart; and
 wherein the at least one value indicative of the patient's arterial blood pressure is/are indicative of diastolic pressure (DP), systolic pressure (SP), pulse pressure (PP), mean arterial pressure (MAP), a change in DP, a change in SP, a change in PP and/or a change in MAP.

25. The implantable monitoring device of claim 24, wherein the arterial blood pressure monitor is configured to:
 determine a peak pulse arrival time (PPAT) by determining an average of the times $t_1$ and $t_2$; and
 determine a value indicative of systolic pressure (SP) based on the PPAT.

26. A non-implantable monitoring device to monitor a patient's arterial blood pressure, the device comprising:
 surface electrodes configured to obtain a surface electrocardiogram (ECG) that is indicative of electrical activity of the patient's heart;
 a non-implantable plethysmography sensor configured to obtain a plethysmography signal indicative of changes in the patient's arterial blood volume;
 an arterial blood pressure monitor configured to
  detect a predetermined feature of the surface ECG signal indicative of ventricular depolarization,
  detect a predetermined feature of the surface ECG signal indicative of ventricular repolarization,
  detect a predetermined feature of the plethysmography signal,
  determine a time $t_1$ from the predetermined feature of the surface ECG indicative of ventricular depolarization to the predetermined feature of the plethysmography signal,
  determine a time $t_2$ from the predetermined feature of the surface ECG indicative of ventricular repolarization to the predetermined feature of the plethysmography signal, and
  determine at least one value indicative of the patient's arterial blood pressure based on the times $t_1$ and $t_2$ determined from the surface ECG signal and plethysmography signal.

27. The non-implantable monitoring device of claim 26, further comprising a housing within which the arterial blood pressure monitor is located;

wherein the surface electrodes are substantially flush with and/or adjacent to the housing;

wherein the plethysmography sensor comprises a photoplethysmography (PPG) sensor configured to obtain a photoplethysmography (PPG) signal indicative of changes in arterial blood volume; and wherein the PPG sensor comprises a light source and a light detector that are within, integral with or attached to the housing.

28. The non-implantable monitoring device of claim 26, further comprising a housing within which the arterial blood pressure monitor is located;

wherein the surface electrodes are remote from the housing and at least some of the surface electrodes are configured to be mounted on skin outside of a patient's rib cage;

wherein the plethysmography sensor comprises a photoplethysmography (PPG) sensor configured to obtain a photoplethysmography (PPG) signal indicative of changes in arterial blood volume; and wherein the PPG sensor comprises a light source and a light detector that are remote from the housing.

29. The non-implantable monitoring device of claim 26, wherein the arterial blood pressure monitor is configured to:

determine a peak pulse arrival time (PPAT) by determining an average of the times $t_1$ and $t_2$; and determine a value indicative of systolic pressure (SP) based on the PPAT.

* * * * *